(12) United States Patent
Leimkuehler, Jr. et al.

(10) Patent No.: US 12,064,619 B2
(45) Date of Patent: Aug. 20, 2024

(54) SYSTEMS AND METHODS RELATED TO INTRAORAL ELECTRICAL STIMULATION

(71) Applicant: BIOLECTRICS LLC, Cleveland, OH (US)

(72) Inventors: William J. Leimkuehler, Jr., Avon, OH (US); Steven W. Cornelius, Rocky River, OH (US); David J. Corn, Cleveland, OH (US); David Mandel, Alexandria, VA (US); Paul Gancitano, Washington, DC (US)

( * ) Notice: Subject to any disclaimer, the term of this patent is extended or adjusted under 35 U.S.C. 154(b) by 0 days.

(21) Appl. No.: 18/159,184

(22) PCT Filed: Jul. 28, 2021

(86) PCT No.: PCT/US2021/043503
§ 371 (c)(1),
(2) Date: Jan. 25, 2023

(87) PCT Pub. No.: WO2022/026579
PCT Pub. Date: Feb. 3, 2022

(65) Prior Publication Data
US 2023/0347139 A1 Nov. 2, 2023

Related U.S. Application Data

(60) Provisional application No. 63/057,887, filed on Jul. 28, 2020.

(51) Int. Cl.
*A61N 1/05* (2006.01)
*A61C 19/06* (2006.01)
(Continued)

(52) U.S. Cl.
CPC ............ *A61N 1/0548* (2013.01); *A61C 19/06* (2013.01); *A61N 1/205* (2013.01); *A61N 1/36034* (2017.08); *A61C 2204/002* (2013.01)

(58) Field of Classification Search
CPC .................................................... A61N 1/0548
See application file for complete search history.

(56) References Cited

U.S. PATENT DOCUMENTS

| 1,389,662 A | 9/1921 | Irwin |
| 2,103,083 A | 12/1937 | Lynch |

(Continued)

FOREIGN PATENT DOCUMENTS

| CA | 2485767 | 4/2005 |
| EP | 0599786 | 6/1994 |

(Continued)

OTHER PUBLICATIONS

Written Opinion for Application No. PCT/US 21/27699, dated Aug. 2, 2021, 7 pages.

(Continued)

*Primary Examiner* — Michael W Kahelin
(74) *Attorney, Agent, or Firm* — Smith Keane LLP

(57) ABSTRACT

An apparatus and method are used to deliver an electrical current to, through or across gingival tissues of a mouth in order to achieve a number of therapeutic, prophylactic, cosmetic, and or regenerative benefits. These benefits include killing or modifying oral microbes, increasing oral vasodilation, reducing oral biofilm, improving oral blood circulation, reversing oral bone resorption, promoting oral osteogenesis, treating gum recession, and fostering gingival regeneration. Other benefits include the treatment of gingivitis, periodontitis, and oral malodor, and other systemic diseases correlated with oral pathogens. Use of systems and methods according to the present invention may effectively tighten epithelial contact with one or more teeth (e.g., by the junctional epithelium and/or the sulcular epithelium) and/or cause a tightening of the oral epithelium, thereby improving an appearance of a human smile.

18 Claims, 22 Drawing Sheets

(51) Int. Cl.
*A61N 1/20* (2006.01)
*A61N 1/36* (2006.01)

(56) References Cited

U.S. PATENT DOCUMENTS

| | | |
|---|---|---|
| 2,151,738 A | 3/1939 | Buhse |
| D119,035 S | 2/1940 | Lindgren |
| 3,118,450 A | 1/1964 | Freeman et al. |
| 3,207,161 A | 9/1965 | Dietz |
| 3,215,139 A | 11/1965 | Dietz |
| 3,380,446 A | 4/1968 | Martin |
| 3,403,684 A | 10/1968 | Stiebel et al. |
| 3,502,076 A | 3/1970 | Bertolini |
| 4,149,533 A | 4/1979 | Ishikawa |
| 4,153,060 A | 5/1979 | Korostoff et al. |
| 4,175,565 A | 11/1979 | Chiarenza et al. |
| D256,958 S | 9/1980 | Markham |
| 4,244,373 A | 1/1981 | Nachman |
| 4,378,007 A | 3/1983 | Kachadourian |
| 4,509,519 A | 4/1985 | Detsch |
| 4,802,444 A | 2/1989 | Markham et al. |
| 4,854,865 A | 8/1989 | Beard et al. |
| D307,339 S | 4/1990 | Markham et al. |
| D308,122 S | 5/1990 | Markham et al. |
| 4,924,811 A | 5/1990 | Axelrod |
| 4,924,880 A | 5/1990 | O'Neill et al. |
| 5,034,847 A | 7/1991 | Brain |
| 5,131,383 A | 7/1992 | Juarez |
| 5,207,231 A | 5/1993 | Fakhri |
| RE34,352 E | 8/1993 | Markham et al. |
| 5,263,436 A | 11/1993 | Axelrod |
| D344,161 S | 2/1994 | Markham |
| 5,284,161 A | 2/1994 | Karell |
| D349,786 S | 8/1994 | Markham |
| 5,339,771 A | 8/1994 | Axelrod |
| 5,372,501 A | 12/1994 | Shalvi |
| 5,433,735 A | 7/1995 | Zanakis et al. |
| 5,490,520 A | 2/1996 | Schaefer et al. |
| D368,339 S | 3/1996 | O'Rourke et al. |
| 5,496,256 A | 3/1996 | Bock et al. |
| 5,725,377 A | 3/1998 | Lemler et al. |
| 5,741,500 A | 4/1998 | Yates |
| 5,792,067 A | 8/1998 | Karell |
| 5,832,877 A | 11/1998 | Markham |
| 5,857,431 A | 1/1999 | Peterson |
| 5,865,146 A | 2/1999 | Markham |
| D407,868 S | 3/1999 | Axelrod |
| 5,947,061 A | 9/1999 | Markham et al. |
| 6,006,130 A | 12/1999 | Higo et al. |
| 6,067,941 A | 5/2000 | Axelrod |
| 6,212,435 B1 | 4/2001 | Lattner et al. |
| 6,212,535 B1 | 4/2001 | Weikart et al. |
| 6,254,391 B1 | 7/2001 | Darnell |
| 6,265,391 B1 | 7/2001 | Herbert |
| 6,405,681 B1 | 6/2002 | Ward |
| 6,415,740 B1 | 7/2002 | Curry |
| 6,439,166 B1 | 8/2002 | Markham |
| D462,487 S | 9/2002 | Axelrod |
| 6,546,896 B1 | 4/2003 | Markham |
| 6,615,766 B1 | 9/2003 | Curry |
| D504,748 S | 5/2005 | Jager |
| 7,018,345 B2 | 3/2006 | Mori et al. |
| 7,044,737 B2 | 5/2006 | Fu |
| 7,087,260 B2 | 8/2006 | Axelrod |
| 7,111,587 B2 | 9/2006 | Rautenbach |
| 7,118,377 B2 | 10/2006 | Inoue et al. |
| 7,163,399 B2 | 1/2007 | Kajimoto et al. |
| D539,430 S | 3/2007 | Lowsky, Jr. et al. |
| RE39,563 E | 4/2007 | Markham |
| D544,655 S | 6/2007 | Hass |
| RE40,430 E | 7/2008 | Markham |
| D579,157 S | 10/2008 | Edwards |
| 7,640,894 B2 | 1/2010 | Jager |
| 7,775,795 B2 | 8/2010 | Khawaled et al. |
| D626,706 S | 11/2010 | Ragonetti |
| 7,874,294 B2 | 1/2011 | Burger |
| 7,886,398 B2 | 2/2011 | Morita et al. |
| 7,890,164 B2 | 2/2011 | Akiyama et al. |
| 7,917,223 B2 | 3/2011 | Madjar et al. |
| D638,589 S | 5/2011 | Axelrod et al. |
| 8,060,220 B2 | 11/2011 | Liebergesell et al. |
| D658,825 S | 5/2012 | Wolfe, Jr. et al. |
| 8,225,747 B2 | 7/2012 | Markham et al. |
| 8,276,547 B2 | 10/2012 | Markham |
| D677,439 S | 3/2013 | Renforth |
| 8,393,300 B2 | 3/2013 | Markham et al. |
| 8,479,750 B2 | 7/2013 | Schaefer et al. |
| D688,836 S | 8/2013 | Costello |
| D689,155 S | 9/2013 | Jahns |
| 8,660,669 B2 | 2/2014 | Nemeh et al. |
| 10,213,598 B2 | 2/2019 | Nemeh et al. |
| 2001/0012608 A1 | 8/2001 | Darnell |
| 2003/0079693 A1 | 5/2003 | Jager |
| 2003/0144625 A1 | 7/2003 | Sherman et al. |
| 2004/0116964 A1 | 6/2004 | Mori et al. |
| 2004/0137118 A1 | 7/2004 | Axelrod |
| 2004/0138646 A1 | 7/2004 | Walla |
| 2004/0186418 A1 | 9/2004 | Karashima |
| 2005/0037311 A1 | 2/2005 | Bergersen |
| 2005/0203587 A1 | 9/2005 | Liebergesell |
| 2006/0178703 A1 | 8/2006 | Huston et al. |
| 2006/0201446 A1 | 9/2006 | Edwards |
| 2006/0271148 A1 | 11/2006 | Liebergesell et al. |
| 2007/0066932 A1 | 3/2007 | Akiyama et al. |
| 2007/0083147 A1 | 4/2007 | Smith |
| 2007/0106138 A1 | 5/2007 | Beiski et al. |
| 2007/0154414 A1 | 5/2007 | Bonfiglio |
| 2007/0191757 A1 | 8/2007 | Steiner et al. |
| 2007/0203389 A1 | 8/2007 | Bergman |
| 2007/0224572 A1 | 9/2007 | Jon |
| 2007/0224898 A1 | 9/2007 | DeAngelis et al. |
| 2007/0259316 A1 | 11/2007 | Conrad et al. |
| 2008/0003540 A1 | 1/2008 | Khawaled et al. |
| 2008/0233541 A1 | 9/2008 | De Vreese et al. |
| 2008/0280248 A1 | 11/2008 | Pitts et al. |
| 2008/0314333 A1 | 12/2008 | Hurwitz |
| 2009/0117513 A1 | 5/2009 | Nemeh et al. |
| 2009/0210032 A1 | 8/2009 | Beiski et al. |
| 2010/0224138 A1 | 9/2010 | Axelrod et al. |
| 2010/0286590 A1 | 11/2010 | Durand |
| 2011/0039226 A1 | 2/2011 | Armanino |
| 2011/0117515 A1 | 5/2011 | Jablow |
| 2011/0179851 A1 | 7/2011 | Mack et al. |
| 2011/0289707 A1 | 12/2011 | Schaefer et al. |
| 2012/0156648 A1 | 6/2012 | Kaufman et al. |
| 2012/0256750 A1 | 10/2012 | Novak |
| 2012/0272922 A1 | 11/2012 | Axelrod et al. |
| 2013/0072851 A1 | 3/2013 | Doll et al. |
| 2013/0209964 A1 | 8/2013 | Nemeh et al. |
| 2014/0023983 A1* | 1/2014 | Lowe .................. A61C 7/008 433/2 |
| 2015/0044628 A1 | 2/2015 | Flyash |
| 2017/0216584 A1 | 8/2017 | Chun et al. |
| 2017/0354808 A1 | 12/2017 | Heikenfeld et al. |

FOREIGN PATENT DOCUMENTS

| | | |
|---|---|---|
| EP | 1525857 | 4/2005 |
| KR | 200362377 | 9/2004 |
| WO | 1979/001082 | 12/1979 |
| WO | 1992/005753 | 4/1992 |
| WO | 2005/062710 | 7/2005 |
| WO | 2006/018525 | 2/2006 |
| WO | 2014/149287 | 9/2014 |
| WO | 2015123292 | 8/2015 |
| WO | 2019147823 | 8/2019 |

OTHER PUBLICATIONS

Int'l Preliminary Report on Patentability for Application No. PCT/US 21/27699, dated May 9, 2022, 10 pages.
USPTO Office Action dated Jun. 25, 2008 regarding U.S. Appl. No. 11/850,661, 8 pages.

(56) References Cited

OTHER PUBLICATIONS

USPTO Office Action dated Apr. 7, 2015 regarding U.S. Appl. No. 13/839,513, 18 pages.
International Search Report and Written Opinion of the ISA dated Feb. 18, 2015, issued in International Application Serial No. PCT/US2014/016710 filed Feb. 17, 2014.
USPTO Office Action dated May 13, 2016 regarding U.S. Appl. No. 15/099,005; 13 pages.
USPTO Office Action dated Aug. 8, 2016 regarding U.S. Appl. No. 14/922,698, 5 pages.
Swayam Chintamami, Examination report No. 1 for standard patent application No. 2014238291, dated Mar. 6, 2018, 3 pages.
Swayam Chintamani, Examination report No. 1 for standard patent application No. 2019201530, dated Mar. 5, 2019, 3 pages.
International Search Report and Written Opinion of the ISA dated Aug. 9, 2019, issued in International Application Serial No. PCT/US19/14969 filed Jan. 24, 2019.
JPO Office Action for Application 2020-562075, dated Jan. 31, 2023, 6 pages.
Written Opinion for Application No. PCT/US 21/43503, dated Jan. 20, 2022, 5 pages.
International Search Report for Application No. PCT/US 21/43503, dated Jan. 20, 2022, 4 pages.
Matsunaga, T. et al., Electrode System for the Determination of Microbial Populations, Applied and Environmental Microbiology, vol. 37 No. 1, Jan. 1979, p. 117-121.
Caubet, R., et al., A Radio Frequency Electric Current Enhances Antibiotic Efficacy . . . , Antimicrobial Agents and Chemotherapy, vol. 48, No. 12, Dec. 2004, pp. 4662-4664.
Giladi, M., et al., Microbial Growth Inhibition by Alternating Electric Fields, Antimicrobial Agents and Chemotherapy, vol. 52, No. 10, Oct. 2008, pp. 3517-3522.
Del Pozo, J.L., et al., The Electricidal Effect is Active in an Experimental Model . . . , Antimicrobial Agents and Chemotherapy, vol. 53, No. 10, Oct. 2009, pp. 4064-4068.
Del Pozo, J.L., et al., Effect of Electrical Current on the Activities of Antimicrobial Agents . . . Antimicrobial Agents and Chemotherapy, vol. 53, No. 1, Jan. 2009, pp. 35-40.
Del Pozo, J.L., et al., The Electricidal Effect: Reduction of *Staphylococcus* . . . , Antimicrobial Agents and Chemotherapy, vol. 53, No. 1, Jan. 2009, pp. 41-45.
Davidovitch, Z., et al., Effect of electric currents on gingival cyclic nucleotides in vivo (Abstract). Journal of Periodontal Research, 1980, 15: 353-362.
Hashimoto, H., Effect of micro-pulsed electricity on experimental tooth movement (Abstract). Nihon Kyosei Shika Gakkai Zasshi, Aug. 1990, 49(4):352-61.
Horning, GM., et al., The prevalence of periodontitis in a military treatment problem (Abstract). J Am Dent Assoc., Nov. 1990, 121(5):616-22.
Onkormanyzat, F., et al., The use of iontophoresis in dental practice (Abstract). Fogorv Sz. Jun. 1993, 86(6):205-12.
Wang, Q., et al., Osteogenesis of electrically stimulated bone cells mediated in part by calcium ions (Abstract), Clin Orthop Relat Res. Mar. 1998, (348):259-68.
Davidovitch, Z, et al., Electric currents, bone remodeling, and orthodontic tooth movement. II. Increase in rate of tooth . . . (Abstract), Am J Orthod, Jan. 1980, 77(1):33-47.
Buch, F., et al., Direct current influence on bone formation in titanium implants (Abstract). Biomaterials, Nov. 1984, 5(6):341-6.
Puhar, I., et al., Efficacy of electrical neuromuscular stimulation in the treatment of chronic periodontitis. J Periodontal Implant Sci 2011; 41:117-122.
Bolton, L., et al., Direct-Current Bactericidal Effect on Intact Skin. Antimicrobial Agents and Chemotherapy, Jul. 1980, vol. 18, No. 1, pp. 137-141.
Ehrlich, G.D., et al., Engineering Approaches for the Detection and Control of Orthopaedic Biofilm Infections, Clin Orthop Relat Res. Aug. 2005, (437):59-66.

Matl, FD., et al., Augmentation of antibiotic activity by low-frequency electric . . . (Abstract). Bioelectromagnetics, Jul. 2011, 32(5):367-77.
Sandhu, SP., et al., Comparative evaluation of different strengths of electrical current . . . (Abstract). Indian J Dent Res. Apr.-Jun. 2010;21(2):207-12.
Kaynak, D., et al., A histopathologic investigation on the effects of electrical stimulation . . . (Abstract). J Periodontol, Dec. 2005, 76(12):2194-204.
Hagiwara, T., et al., Effect of electrical stimulation on mandibular distraction osteogenesis (Abstract). J Craniomaxillofac Surg, Feb. 2000, 28(1):12-9.
Chakkalakal, DA., et al., Electrophysiology of direct current stimulation of fracture . . . (Abstract). IEEE Trans Biomed Eng., Nov. 1990, 37(11):1048-58.
Kane, WJ. Direct current electrical bone growth stimulation for spinal fusion (Abstract). Spine (Phila Pa 1976), Mar. 1988, 13(3):363-5.
Periodontal Disease Fact Sheet, American Academy of Periodontology, www.perio.org/newsroom/periodontal-disease-fact-sheet, Oct. 10, 2013.
Manuelderegil@xxxxxxxxx. "Perioprotect ripoff", perioprotect.ripoff, Mar. 20, 2009.
Petersen, P.E., et al., Strengthening the prevention of periodontal disease: the WHO approach, J Periodontol, Dec. 2005, vol. 76, No. 12, pp. 2187-2193.
Pitman, S., US Army develops tooth-cleaning gum, Cosmetics design.com, Dec. 21, 2005.
Bloomberg Businessweek, Why P&G's Smile is So Bright, Jul. 31, 2002, 4 pages.
Hitti, M., 9 Risk Factors for Tooth Loss, WebMD.com, Nov. 11, 2005, 3 pages.
American Dental Association, Key Dental Facts, Sep. 2008, 26 pages.
Karolefski, J., Changing Habits. Supermarket News., Feb. 16, 2009, http://supermarketnews.com/print/nonfood/changing-habits, 4 pages.
Dental Managment: Cost of Deep Perio Cleaning from a Dentist . . . Oct. 10, 2013, http://thewealthydentist.com/SurveyResults/119-Perio-Cleaning.htm, 2 pages.
Johnsen, M., 2009 Hot Products: Editor's Picks. Drug Store News, Jun. 2009, www.drugstorenews.com, 17 pages.
Ichimura, K., et al., Effect of weak electric current on reducing oral bacteria in vitro. Bull. Tokyo dent. Coll., vol. 42, No. 2, pp. 97-100, May 2001.
Poortinga, A.T., et al., Electric field induced desorption of bacteria from a conditioning film covered substratum. Biotechnology and Bioengineering, vol. 76(4):395-99 Dec. 2001.
Glazer, P.A., et al., Electricity: The history and science of bone growth stimulation for spinal fusion. The Orthopaedic Journal at Harvard Medical School, 2002, pp. 63-67.
Albandar, J.M., et al., Gingival recession, gingival bleeding, and dental calculus in adults 30 years of age and older . . . J Periodontol, Jan. 1999, vol. 70, No. 1, pp. 30-43.
Banga, A.K., et al., Iontophoresis and electroporation: comparisons and contrasts. International Journal of Pharmaceutics 179 (1999) pp. 1-19.
Piekarski, K., et al., Osteogenetic stimulation by externally applied DC current. Acta Orthop. Scand. vol. 49, pp. 113-120, 1978.
Hartshorne, E. On the causes and treatment of pseudarthrosis and especially that form of it sometimes called supernumerary joint. Am J Med, Jan 1841; vol. 1; pp. 121-156.
Tronstad et al., "Effect of Electric Current and Silver Electrodes on Oral Bacteria", Endod Dent Traumatol 1985; 1:112-115.
Guthmiller et al., Chapter 8—Peridontal Diseases (pp. 1-19), Polymicrobial Disease, (Washington (DC); ASM Press; 2002).
Gaitte-Jardim Junior et al, "Microbiota Associated with Chronic Osteomyelitis of the Jaw," Brazilian Journal of Microbiology, vol. 41, No. 4, Sao Paulo, Oct. /Dec. 2010.
Han et al., "Term Stillbirth Caused by Oral Fusobacterium nucleatum," Obstetrical Gynecology, 2010, 115: 442-5.

(56) References Cited

OTHER PUBLICATIONS

Hintao et al., "The Microbiological Profiled of Saliva, Supragingival and Subgingival Plaque and Dental Caries in Adults with and without Type 2 Diabetes Mellitus," Oral Microbiology Immunology, 2007: 22: 175-181.
USPTO Office Action dated May 24, 2017 regarding U.S. Appl. No. 15/583,194, 7 pages.
Written Opinion of the International Preliminary Examining Authority from corresponding International Application Serial No. PCT/US/2014/016710, dated Apr. 6, 2015.
USPTO Office Action dated Mar. 22, 2012 regarding U.S. Appl. No. 12/205,062, 17 pages.
USPTO Office Action dated Nov. 29, 2012 regarding U.S. Appl. No. 12/205,062, 12 pages.
USPTO Office Action dated Sep. 24, 2013 regarding U.S. Appl. No. 12/205,062, 9 pages.
Kalinowski et al., "Low-Voltage Direct Current as a Fungicidal Agent for Treating Onychomycosis", Journal of the Am. Pod. Med. Assoc. vol. 94, No. 6, Nov./Dec. 2004; pp. 565-572.

\* cited by examiner

| Device State | Treatment Indicator Light | Battery Indicator Light | Audible Feedback Tone/Sequence | Audible Feedback Persistence |
|---|---|---|---|---|
| OFF | Off | Off | 3 falling tones | One time on transition |
| READY | On-White | Off | 3 rising tones (From OFF) 1 tone (From all other states) | One time on transition |
| RUN | On-Blue | Off | 2 rising tones | One time on transition |
| OPEN | Flashing-Blue | Off | 5 rise and 5 fall tones (alternating) | Repeats at 10 second intervals for first 30 seconds, then at 30 second intervals. |
| COMPLETE | Flashing-White | Off | Short melody greater than 2 seconds | One time on transition |
| LOW BATTERY[1] | Off (From READY) Flashing-White (From COMPLETE) | Flashing-Amber | 2 falling tones (From READY) Off (From COMPLETE) | One time on transition / repeat on button press if in READY state |
| CRITICAL BATTERY | Flashing-Red | Flashing-Amber | 4 short tones | One time on transition |
| CHARGING[2] | Off | Flashing-White (charging) On-White for 10 minutes[4] (Charging complete) | 2 rising tones | One time on transition |
| FAULT[3] | Flashing-Red | Off | 4 short tones | One time on transition |
| BLE Paired (Service App) | No change | No change | No change | |

Fig. 11

| Parameter | Description | Default Value | Min Value | Max Value | Increment | Units |
|---|---|---|---|---|---|---|
| UDI_DEVICE_IDENTIFIER | Unique device identifier - Device Identifier | FTPU | 14 | 14 | n/a | Characters (Numeric only) |
| UDI_MANUFACTURING_DATE | Unique device identifier - Manufacturing Date | FTPU | 6 | 6 | n/a | Characters (Numeric only) |
| UDI_SERIAL_NUMBER | Unique device identifier - Serial Number Identifier | FTPU | 6 | 6 | n/a | Characters (Numeric only) |
| PATIENT_ID | Unique ID number | - | - | 100 | n/a | Characters (Numeric only) |
| DENTIST_ID | Unique ID number | - | - | 100 | n/a | Characters (Numeric only) |
| HYGIENIST_ID | Unique ID number | - | - | 100 | n/a | Characters (Numeric only) |
| TREATMENT_DURATION | Duration of current delivery (SRS 3.05) | 1200 | 1 | 1800 | 1 | seconds |
| INACTIVITY_DURATION_READY | Duration of inactivity before powering off when in READY state (SRS 2.03) | 60 | 1 | 1200 | 1 | seconds |
| INACTIVITY_DURATION_OPEN | Duration of inactivity before powering off when in OPEN state. | 300 | 1 | 1200 | 1 | Seconds |
| INACTIVITY_DURATION | Duration of inactivity before powering off in COMPLETE, LOW BATTERY or FAULT states. | 180 | 1 | 1200 | 1 | Seconds |
| CHANNEL_1 | Individual Channels On=1, Off=0 | 1 | 0 | 1 | 1 | - |
| CHANNEL_2 | Individual Channels On=1, Off=0 | 1 | 0 | 1 | 1 | - |
| CHANNEL_3 | Individual Channels On=1, Off=0 | 1 | 0 | 1 | 1 | - |
| CHANNEL_4 | Individual Channels On=1, Off=0 | 1 | 0 | 1 | 1 | - |
| CHANNEL_5 | Individual Channels On=1, Off=0 | 1 | 0 | 1 | 1 | - |
| CHANNEL_6 | Individual Channels On=1, Off=0 | 1 | 0 | 1 | 1 | - |
| CHANNEL_7 | Individual Channels On=1, Off=0 | 1 | 0 | 1 | 1 | - |

Fig. 12A

| Parameter | Description | Default Value | Min Value | Max Value | Increment | Units |
|---|---|---|---|---|---|---|
| CHANNEL_8 | Individual Channels On=1, Off=0 | 1 | 0 | 1 | 1 | -- |
| POWER_MODE | Power mode in OFF state, Low Power Mode=1, Power Off Mode=0 | 1 | 0 | 1 | 1 | -- |
| MIN_CURRENT_PERCENT | Percentage of minimum total current threshold based on the sum of the target current for all currently enabled channels | 75 | 0 | 100 | 1 | % |
| MIN_CURRENT_TIME | Duration for which the sum of total current across all channels is below the MIN_CURRENT_PERCENT of target to trigger an efficacy fault | 30 | 1 | 120 | 1 | seconds |

Fig. 12B

| Reference | Counter | Description | Increment Condition | Reset Condition | Cleared by User Reset |
|---|---|---|---|---|---|
| 1 | Manual Power Ons | Number of times the device has been powered on using the push-button. | Transition from OFF to READY states | Firmware Update | Yes |
| 2 | Automatic Power Ons | Number of times the device transitions to READY without a button press | Removed from the charger; transition from CHARGING to READY | Firmware Update | Yes |
| 3 | Manual Power Offs | Number of times the device has been powered off using the push-button. | Transition to OFF from READY, COMPLETE, RUN, OPEN, LOW BATTERY, or FAULT states by push-button press. | Firmware Update | Yes |
| 4 | Automatic Power Offs | Number of times the device powered off due to being removed from the charging base or inactivity before or after a treatment | Transition to OFF due to inactivity in the READY, COMPLETE, OPEN, LOW BATTERY, CRITICAL_BATTERY or FAULT states | Firmware Update | Yes |
| 5 | Critical Battery Power Offs | Number of times the device entered the CRITICAL_BATTERY state. | Transition from any state to CRITICAL BATTERY | Firmware Update | Yes |
| 6 | Recharges Initiated | Number of times that the user placed the device onto the charging base | Transition to CHARGING state | Firmware Update | Yes |
| 7 | Completed recharges | Number of times charging was completed | Charging chip indicates to micro that charging is complete | Firmware Update | Yes |
| 8 | Treatments Started | Number of times the user started a treatment | Transition from READY to RUN states | Firmware Update | Yes |
| 9 | Successfully Completed Treatments | Number of times the user completed a treatment | Transition from RUN to COMPLETE states | Firmware Update | Yes |
| 10 | Open Circuits | Number of times open circuit conditions occurred | Transition from RUN to OPEN states | Firmware Update | Yes |
| 11 | Low Battery | Number of times low battery occurred | Transition to LOW BATTERY states | Firmware Update | Yes |
| 12 | Faults | Number of times faults occurred | Transition to FAULT state | Firmware Update | Yes |
| 13 | Efficacy Faults | Number of times an efficacy fault occurred | Transition to FAULT state from RUN state due to total current delivered being less than MIN_CURRENT_PERCENT of target | Firmware Update | Yes |
| 14 | Overcurrent Faults | Number of times a fault occurred due to overcurrent delivery | Transition to FAULT state from RUN state due to an overcurrent condition | Firmware Update | Yes |
| 15 | Total Minutes of Treatment Delivered | Total minutes of treatment delivered | Each minute during RUN state | Firmware Update | Yes |
| 16 | Bluetooth Connects | Number of times Bluetooth device has connected to the device | Each time a Bluetooth connection occurs | Firmware Update | Yes |

Fig. 13A

| Reference | Counter | Description | Increment Condition | Reset Condition | Cleared by User Reset |
|---|---|---|---|---|---|
| 17 | Cumulative Charge | Cumulative charge delivered (µAs) for each channel over the device lifetime. | Increment at the end of each treatment to add cumulative charge delivered on each channel. | Firmware Update | No |
| 18 | Device Uptime | Cumulative time that the device has been powered on over the device lifetime. | Increment anytime the device microprocessor is powered on, including when the device state is OFF in Low Power Mode. | Persists for device lifetime | No |
| 19 | Time Since Power On | Cumulative time that the device has been powered on since the last microprocessor power off. | Increment anytime the device microprocessor is powered on, including when the device state is in Low Power Mode. | Resets on each microprocessor power off into OFF State | No |

Fig.13B

| Recorded Events | Event Data | Description |
|---|---|---|
| Power On | [Automatic, Manual] | Transition from OFF to READY; transition from CHARGING to READY (automatic) |
| Treatment Started | [Voltage Levels for all channels] | Transition from READY to RUN |
| Battery Level (Start) | [Battery Voltage Level] | Battery level on transition from READY to RUN |
| Charge Delivered | [Treatment duration in seconds, Total charge delivered for each channel (coulombs)] | Transition from: RUN to any state other than OPEN; OPEN to any state other than RUN |
| Open Circuit | | Transition from RUN to OPEN |
| Treatment Resumes | | Transition from OPEN to RUN |
| Treatment Completed | [Voltage Levels for all Channels] | Transition from RUN to COMPLETE; voltage should be recorded just prior to transitioning from RUN state while current is still being delivered |
| Battery Level (Completed) | [Battery Voltage Level] | Battery level on transition from RUN to COMPLETE |
| Power Off | [Type: Inactivity, Button Press, Critical Battery] | Transition to OFF |
| Low Battery | [Battery Voltage Level] | Transition to LOW BATTERY |
| Critical Battery | [Battery Voltage Level] | Transition to CRITICAL BATTERY |
| Charging Initiated | [Battery Voltage Level] | Transition to CHARGING |
| Charging Complete | | Charging chip signals to micro that battery charging is complete |
| Overcurrent Fault | [Current level for all channels, Voltage level for all channels] | Transition to FAULT due to overcurrent condition |
| Efficacy Fault | [Voltage Levels for all channels, Current Level for all channels] | Transition to FAULT state from RUN state due to total current delivered being less than MIN_CURRENT_PERCENT of target |
| Other Fault | [Fault Code] | Transition to FAULT for reasons other than lack of efficacy, critical battery or overcurrent |
| Bluetooth Device Connected | [MAC Address of iPad] (if available) | Each time a Bluetooth device connects successfully |
| Bluetooth Device Disconnected | [MAC Address of iPad] (if available) | Each time a connected Bluetooth device disconnects |
| Current Date & Time | [Current date and time; precision of at least 1 second] | Upon receipt of the date and time from a Bluetooth device (e.g. Service App) |

Fig. 14

| Operating Function | User Task(s) | Device Response |
|---|---|---|
| *High level operating functions that involve user interaction with the device* | *One or more user interactions with a device to achieve a desired result* | *Device interaction to complete the task (from the user's perspective)* |
| 1  Prepare device for use | 1.1  Remove device from packaging (first time use), carrying case, or charger | (If removed from charger and device is powered on) Device gives user audible and visual indication that device is ready to start a treatment. The device plays a tone and the treatment indicator light turns on (white) |
| 2  Power on | 2.1  (If needed) Press and hold the button to turn on device | Device powers on, gives user audible and visual indication that the device is ready to start a treatment. The device plays a tone and the treatment indicator light turns on (white). |
| 3  Insert mouthpiece into mouth | 3.1  Insert the mouthpiece into the mouth | None |
| 4  Perform treatment | 4.1  Press the button to start the treatment | Device gives audible and visual indication of starting treatment. The device plays a series of tones and the treatment indicator light changes to blue (on). Device begins delivering current and timing treatment duration. |
|  | 4.2  (If needed) Temporarily remove/reinsert the mouthpiece during treatment | Device pauses/resumes treatment and gives audible and visual indication. While paused, the device plays a series of tones (repeating periodically) and the treatment indicator light changes to flashing blue. When treatment resumes, the device plays a series of tones and the treatment indicator light changes to blue (on). |
|  | 4.3  Wait for treatment to complete | Device completes current delivery cycle and gives No audible and visual indication |

Fig.15A

| Operating Function | | User Task(s) | | Device Response |
|---|---|---|---|---|
| | | | | that the treatment is complete. The device plays a series of tones and the treatment indicator light changes to flashing white |
| 5 | Remove mouthpiece from mouth | 5.1 | Remove the mouthpiece from the mouth | None |
| 6 | Power off | 6.1 | (If needed) Press and hold button to turn off or allow device to automatically turn off after short time | Powers off when user presses and holds button, or automatically turns off after short period of time |
| 7 | Clean mouthpiece | 7.1 | Rinse the mouthpiece with water | None |
| | | 7.2 | optional) If the mouthpiece is not clean, scrub with soft toothbrush and hand soap | None |
| 8 | Charge device | 8.1 | Plug charger into wall outlet | None |
| | | 8.2 | Place device onto the charger | Device indicates charging status via audible and visual indication. The device plays a series of tones and the battery indicator light flashes white, indicating charging (or turns on white indicating charging complete). |
| 9 | Store mouthpiece | 9.1 | (optional) Place the mouthpiece in the carrying case | None |
| 10 | Respond to low battery | 10.1 | Place device onto the charger when the device indicates low battery (see 8.2) | Device indicates low battery condition and charging status via audible and visual indication. The device battery indicator light flashes amber, indicating a low battery condition. When the device is placed on the charger, the device plays a series of tones and the battery indicator light changes |

Fig.15B

| Operating Function | | User Task(s) | | Device Response |
|---|---|---|---|---|
| | | | | to flashing white, indicating charging. |
| 11 | Respond to critical battery | 11.1 | Place device onto the charger when the device indicates critical battery (see 8.2) | Device indicates critical battery condition and charging status via audible and visual indication. The device plays a series of tones and the treatment indicator light changes to flashing red. The battery indicator light flashes amber, indicating a low battery condition. When the device is placed on the charger, the device plays a series of tones, the treatment indicator light turns off, and the battery indicator light changes to flashing white, indicating charging. |
| 12 | Respond to faults | 12.1 | Contact treating dentist for evaluation or a replacement device. | Device indicates fault condition via audible and visual indication. The device plays a series of tones and the treatment indicator light changes to flashing red. |

Fig.15C

SYSTEMS AND METHODS RELATED TO INTRAORAL ELECTRICAL STIMULATION

BACKGROUND

This invention relates to systems and methods related to promoting general oral hygiene or cosmetics, treating periodontal diseases such as gingivitis and periodontitis, killing or modifying oral microbes including cavity-causing bacteria, reducing oral biofilms, increasing blood flow in oral tissues, increasing salivation, promoting gingival tissue regeneration, fostering osteogenesis in the boney structures of the teeth, mouth and related areas, treating systemic diseases associated with oral bacteria, and/or treating other periodontal and oral maladies through the non-invasive application of direct current electricity to the surfaces in the oral cavity, and it also relates to an apparatus suitable for providing direct current electricity for these therapeutic, prophylactic, cosmetic, and regenerative effects.

Periodontal disease has been identified as a risk factor for various systemic diseases by both dentists and physicians. Included in these diseases are cardiovascular disease, adverse pregnancy outcomes, and diabetes with newfound evidence supporting its association with pancreatic diseases and arthritis. While many of the studies establish correlation between the presence of periodontal disease and these systemic conditions, causation, with most of these conditions, is still a subject of ongoing research. A few of the biological mechanisms which have been proposed as to how oral bacteria stemming from periodontal disease can cause systemic disease are as follows:

1. Direct effect of oral infections: Oral microbes and their byproducts can gain systemic access via the circulatory system through traveling through compromised tissue and inflamed periodontium in the oral cavity. In gaining systemic access, oral microbes have the potential to directly influence subclinical mediators of various systemic diseases.

2. Inflammation: People with periodontal disease have elevated levels of systemic inflammatory markers due to the burden of increased levels of oral bacteria. Treatment for periodontal disease has been reported to decrease systemic inflammation levels.

3. Cross-reactivity: The progression of systemic diseases can be accelerated by the immune response to bacterial heat-shock proteins creating antibodies that cross-react with innate heat shock proteins expressed on cells of the damaged tissues.

Cardiovascular Disease

Studies investigating the potential association between periodontal disease and cardiovascular diseases, including atherosclerosis, coronary heart disease, and stroke have found a significant positive correlation between poor oral health and the prevalence of cardiovascular disease. While both diseases share several common risk factors, recent studies suggest that periodontitis may precede and therefore contribute to atherosclerotic complications. In fact, meta-analyses show that subjects suffering from periodontitis experience an increased risk for developing cardiovascular diseases.

While it has not been definitively shown if these bacteria initiate atherosclerosis or rather invade an already compromised artery, antibodies to periodontal bacteria, including *Fuseobacterium nucleatum* and *Streptococcus oralis*, have been found in blood serum and are associated with an increased risk of coronary heart disease. A mouse study found that intravenous inoculation with *Porphyromonas gingivalis* accelerated atherosclerotic development. Further, following oral inoculation, *P. gingivalis* DNA was found in the aortic tissue of those infected mice that showed observable signs of accelerated early atherosclerosis. Another study has named *F. nucleatum* as a synergistic agent with *P. gingivalis*. *F. nucleatum* enhances the ability of *P. gingivalis* to invade host cells due to a coaggregating effect between the two organisms. This is significant as bacteria within the atheroma may lead to the development of atherosclerotic plaque. The evidence thus far supports the idea that periodontitis leads to systemic exposure to oral bacteria which serves as a potential source of systemic inflammatory mediators, cytokines produced in the infected periodontal tissues, capable of initiating or worsening atherosclerosis and coronary heart disease when they enter into the blood stream. Clinical studies on periodontal disease have also revealed a positive association with coronary disease and emphasis is now being placed on understanding the exact relation between periodontal disease and atherosclerosis.

Pre-Term Birth

*Fusobacterium nucleatum*, one of the most prevalent species of bacteria found in amniotic fluid and placental infections that cause preterm birth, is also often named the sole infectious agent in preterm labor with intact fetal membranes. *F. nucleatum* is also highly associated with various types of periodontal disease. During periodontal infection, when the oral mucosa is injured and inflamed and the quantities of periodontal pathogens increase dramatically, transient levels of bacteria can appear in the blood leading to selective colonization of undesired sites. One study demonstrated that pregnant mice injected hematogenously with *F. nucleatum* isolated from either amniotic fluid infection or an oral source resulted in fetal death.

Recently, a human stillbirth case was analyzed and it was found that the *F. nucleatum* did indeed originate from the mother's oral cavity, a fact that had not yet been proven. It is likely that the *F. nucleatum* translocated from the mother's mouth via the blood stream where it was then able to cross the endothelium to proliferate and colonize within the fetal membranes, amniotic fluid and fetus whereupon its presence lead to fetal demise. In a mouse model, hematogenous injection of *F. nucleatum* into pregnant mice resulted in specific bacterial colonization in the placenta causing localized inflammation. *F. nucleatum* was completely cleared from the maternal circulation after 24 hours of injection. However, once colonized in the immune privileged placenta, the bacteria proliferated quickly and caused fetal death within 3 days. Chronic periodontal disease could mediate infection through the translocation of periodontal bacteria/inflammatory markers to the fetoplacental unit.

Diabetes

Diabetes mellitus is an endocrine disease that stems from genetic, environmental and behavioral risk factors. For the past several decades, diabetes has been considered a modifying factor for periodontal disease with recent years suggesting a bidirectional relationship between the two. Further, presence of periodontal disease has been implicated as a risk for diabetic complications, namely poor glycemic control. Recent longitudinal and systemic studies have seen periodontal disease correlated to higher risks of death from ischemic heart disease, diabetic nephropathy, end-stage renal disease and increased insulin resistance compared to patients with mild or no periodontal disease. In type II diabetes, insulin resistance is linked to the actions of pro-inflammatory cytokines. It is believed that periodontal disease leads to a significantly higher amount of these serum markers of inflammation, thus conferring insulin resistance. A human study examining the bacterial content of adults with and without type II diabetes found diabetic patients had significantly more severe periodontitis and higher levels of many oral bacteria, including *Streptococcus oralis*.

Pyogenic Liver Abscess

*F. nucleatum* has recently been implicated in pyogenic liver abscess (PLA). Normally caused by biliary tract pathology, diverticular disease and bowel malignancy, atrophic gastritis and cryptogenic liver disease, PLA caused by *F. nucleatum* is very rare with *Escherichia coli, Klebsiella* and *Enterobacter* being the most commonly isolated microorganisms in the drained abscesses. *F. nucleatum* was found in the liver abscess with no other infectious source being found, except for a dental extraction. It is hypothesized that due to the coaggregation properties of *F. nucleatum*, it is able to transport and breach the mucosa of the colon and lead to bacteremia which results in hepatic abscess.

Osteomyelitis

Osteomyelitis is a bone infection caused by bacteria, fungi or other germs. Commonly, bacteria spreads to the bone from infected skin, muscles or tendons and often time occur under a skin sore. The infection can also start in another part of the body and spread hematogenously. Occasionally *Fusobacterium* species have been isolated from bone/joint infections in the head and neck area and were associated with chronic periodontitis. A recent study has reported a case of osteomyelitis caused by *F. nucleatum* in conjunction with muscle abscess. The patient had no known predisposing factors and had no other infection sources except a history of periodontal disease. It is believed that due to the patient's poor oral hygiene, *F. nucleatum* bacteremia may have developed and lead to a hematogenous osteomyelitis of the lower leg.

Arthritis

Numerous clinical studies have suggested a potential association between rheumatoid arthritis (RA) and periodontal disease as several oral bacteria species, such as *P. gingivalis* and *Prevotella intermedia*, have been isolated from the synovial fluid of patients. Periodontal disease is thought to allow bacteria to penetrate through the permeable pocket epithelial in the oral cavity to reach the underlying gingival connection tissue. From there, it may be transported out into the bloodstream with the ability to colonize elsewhere within the body. The oral bacteria found in the synovial fluid of patients suffering from RA has been attributed to synovial inflammation favorably trapping oral bacteria DNA, which suggests periodontal disease may have a perpetuating effect on joint diseases. Therefore, periodontitis may in fact be a factor leading to the autoimmune inflammatory responses characteristic of RA. Patients suffering from RA may also be at a higher risk of developing periodontal disease thus suggesting a bidirectional relationship between the two conditions. One particular study examined the presence of bacterial DNA in the synovial fluids of native and failed prosthetic joints of patients suffering from arthritis. Out of the 5 patients where bacterial DNA was found, *F. nucleatum* was detected in 4 of these 5 patients. This suggests that this bacterium can translocate from the oral cavity to the synovial fluid, as *F. nucleatum* was also found in the patient's plaque sample.

Oral Biofilm

Periodontitis, gingivitis, and caries are infectious diseases of the oral cavity in which oral biofilm and bacteria plays a causative role. Biofilm formation is also involved in the pathogenesis of dental implant failures such as peri-implantitis, denture stomatitis, and oral yeast infections such as candidiasis. Oral biofilms begin with dental pellicle formation on the teeth. This pellicle is composed of salivary proteins that coat the exposed surfaces of the teeth, primarily the supra-gingival ones, to which the planktonic bacteria begin to adhere. The aerobic bacteria, including gram-positive cocci, such as *S. oralis*, are the early colonizers that begin forming the initial biofilm colony, primarily through cellular division of the adherent bacteria.

Once the initial colony has been established, other co-aggregating bacteria species, such as *F. nucleatum, P. gingivalis*, and other gram-negative, anaerobic bacteria attach to the previously formed colonies. As these colonies mature, they grow to cover the sub-gingival surfaces of the teeth and begin to induce inflammation in the periodontium.

SUMMARY OF THE INVENTION

The present invention relates to a method and apparatus for aiding overall oral health and/or cosmetic appearance, and more particularly to treating periodontal diseases such as gingivitis, periodontitis, and peri-implantitis; killing oral microbes including cavity-causing bacteria; reducing oral biofilms; increasing blood flow in oral tissues; increasing salivation; promoting gingival tissue regeneration; fostering osteogenesis in the boney structures of the teeth, mouth, and related areas; treating systemic diseases associated with oral bacteria; and treating other periodontal and oral maladies through the non-invasive application of weak electricity to the surfaces in the oral cavity. Alternatively or additionally, use of embodiments of systems and methods according to the present invention can lead to a reduction of periodontal pocket depth, a reduction of gingival bleeding, a reduction of gingival inflammation and/or a reduction in clinical attachment loss. Use of systems and methods according to the present invention has also been found to effectively tighten epithelial contact with one or more teeth (e.g., by the junctional epithelium and/or the sulcular epithelium) and/or cause a tightening of the oral epithelium, thereby improving an appearance of a person's smile.

These effects are accomplished by the delivery of electrical (preferably direct) current to the gingiva through a plurality of electrodes in direct physical (or at least electrical) contact with gingival tissue surfaces (e.g., lingual, buccal, palatal, and/or vestibular gingival tissue). The electrodes may be fashioned out of any electrically-conductive material, including but not limited to metals such as silver, stainless steel, copper, gold, platinum, palladium, aluminum, an alloy thereof, electrically-conductive nanotubes, carbonized rubber, electrically-conductive silicone, or electrically-conductive polymers. Each electrode may be composed of the same material as one or more of the other electrodes or it may be composed of a different material than one or more of the other electrodes. These electrodes fit snuggly against, or proximate to, the lingual and buccal sides of the gingiva and make electrical (e.g., physical or spaced from but in electrical) contact with each side (i.e., lingual and buccal) or the same side (i.e., lingual or buccal) of the gingiva to pass electricity across or along the teeth and neighboring gingival tissues.

The electrodes on each side (lingual or buccal) of the gingiva along one or more teeth may be of the same polarity. Electrodes on opposite sides of the gingiva may be the opposite polarity, or adjacent electrodes on the same side of the gingiva may be opposite polarity. This allows the current to flow across and/or along the teeth and gums to the electrodes positioned on the transverse gingiva to complete the electrical circuit. Put another way, all electrodes on the lingual side of the gingiva may be completely anodic or completely cathodic. All electrodes on the buccal surfaces of the gingiva, transverse the lingual surfaces of the gingiva, may then have the opposite polarity of the lingual electrodes. The polarization of these electrodes may be reversed during an electrical stimulation session or in between sessions. Electrodes are preferably individually programmable to anode functionality, cathode functionality, or even disconnected or high impedance state. Alternatively, a group of electrodes (e.g., all lingual electrodes) may have fixed functionality as an anode or cathode.

The mandibular and maxillary gingiva each may receive a plurality of electrodes. This allows for stimulation of both the maxillary and mandibular periodontium either simultaneously or in isolation. The maxillary and mandibular sets of electrodes may be powered by two different adjustable power supplies or by the same adjustable power supply.

Electrical conductors (which may be wired or more preferably a conductive silicone) connect the electrodes to an adjustable power supply. All of the enabled anodic electrodes will connect to the negative pole of the power supply and all of the enabled cathodic electrodes will connect to the positive pole of the power supply, through a current regulator. The adjustable power supply is capable of delivering a stable, direct current in the approximate range of 1 to 500 microamperes. The preferred current setting for most stimulation sessions is in the approximate range of 50 to 250 microamperes. More preferably, the current setting is about 125-150 microamperes, controlled to ±10%.

According to an aspect of an embodiment of a system according to the present invention, the system includes a controller and a mouthpiece. The controller has a housing containing a variable direct current power supply, the power supply capable of delivering approximately 1 to 500 microamperes. The mouthpiece configured to be received in a human mouth, the mouthpiece comprising at least one U-shaped channel. A plurality of exposed electrodes may be supported by the mouthpiece and coupled to the direct current power source. A neck portion preferably electrically couples the direct current power supply to the mouthpiece and physically couples the housing to the mouthpiece. The electrical coupling in the neck portion may be achieved by a plurality of electrically conductive pins inserted into and substantially surrounded by traces of electrically conductive silicone.

According to another aspect of an embodiment of a system according to the present invention, a first of the plurality of exposed electrodes is a cathode electrode disposed on a first side of a first of the at least one U-shaped channel and a second of the plurality of exposed electrodes is an anode electrode disposed on a second side of the first channel.

According to still another aspect of an embodiment of a system according to the present invention, the mouthpiece comprises two U-shaped channels, wherein one channel is configured to receive one or more maxillary teeth of a human and the other channel is configured to receive one or more mandibular teeth of the human.

According to yet another aspect of an embodiment of a system according to the present invention, the controller comprises electronic circuitry disposed in the housing, the circuitry being configured to at least one of manipulate and monitor at least one of duration and intensity of current provided by the power source to each electrode. The controller may further include a user input interface and a user feedback interface. The controller also may be configured to store one or more counter values and an event log in non-volatile memory, the event log preferably capable of storing two thousand event occurrences, including a timestamp associated with each.

According to a further aspect of an embodiment of a system according to the present invention, the variable direct current power supply comprises a rechargeable lithium-ion battery. The system may include a charging station capable of physically supporting the controller housing and inductively recharging the rechargeable lithium-ion battery. The charging station may further include a hinged cover, which may contain the controller and mouthpiece, such as for storage and/or travel.

According to still a further aspect of an embodiment of a system according to the present invention, wherein the system further comprises a mobile wireless communication device capable of physical layer communication with the controller, the wireless device further including a software application capable of software layer communication with the controller. The controller is preferably capable of transmitting counter values and an event log to the wireless device the application, such transmission occurring upon at least one of an occurrence of a predetermined event, an expiration of a predetermined time period, and at a predetermined time of day. The application is preferably configured to display simultaneously at least one transmitted counter value and event log and also configured to allow storage of the transmitted counter values and event log to non-volatile memory in the wireless device. The application is also preferably configured to periodically or on-demand provide firmware updates to the controller.

According to yet a further aspect of an embodiment of a system according to the present invention, the mouthpiece may be formed by a process comprising the steps of:
    a first injection molding procedure using the conductive silicone material to form the traces and the electrodes to form a conductive skeleton; and
    a second injection molding procedure using insulative silicone material to encapsulate at least a portion of each trace. The second injection molding procedure is preferably performed after the first injection molding procedure.

According to an aspect of an embodiment of a method according to the present invention, the method includes the steps of:
    providing a mouthpiece supporting a plurality of electrodes coupled to a direct current power source;
    positioning a first electrode of the plurality of electrodes between a cheek and exterior gumline of a human, and in physical contact with gingival tissue;
    positioning a second electrode of the plurality of electrodes medial to the first electrode, and in physical contact with gingival tissue;
    delivering current from the power source to the gingival tissue;
    regulating the intensity of current delivery to the gingival tissues to approximately between 1 and 500 microamperes via a controller; and
    regulating the duration of current delivery to no more than 30 minutes via the controller.

According to another aspect of a method according to the present invention, the method further includes the steps of:
    storing data metrics and an event log in non-volatile memory in the controller;
    providing a software application on an electronic wireless device capable of communicating with the controller;
    pairing the wireless device to allow communications with the controller;

transferring the data metrics and event log from the controller to the wireless device;

saving the data metrics and event log into non-volatile memory of the electronic device; and reviewing at least some of the saved data metrics and event log using the software application.

BRIEF DESCRIPTION OF THE DRAWINGS

FIG. 11 provides a table of user interface feedback occurring at predetermined times in predetermined device or software states.

FIGS. 12A-B provides a table of programmable parameters stored in memory in a controller according to the present invention.

FIGS. 13A-B provides a table of counters or metrics to be logged upon respective occurrence during operation of a controller according to the present invention.

FIG. 14 provides a table of events and associated event data recorded by software FIGS. 15A-C provides a table of operating functions, associated operational user tasks, and responses of a controller according to the present invention.

DETAILED DESCRIPTION

Figure 1:
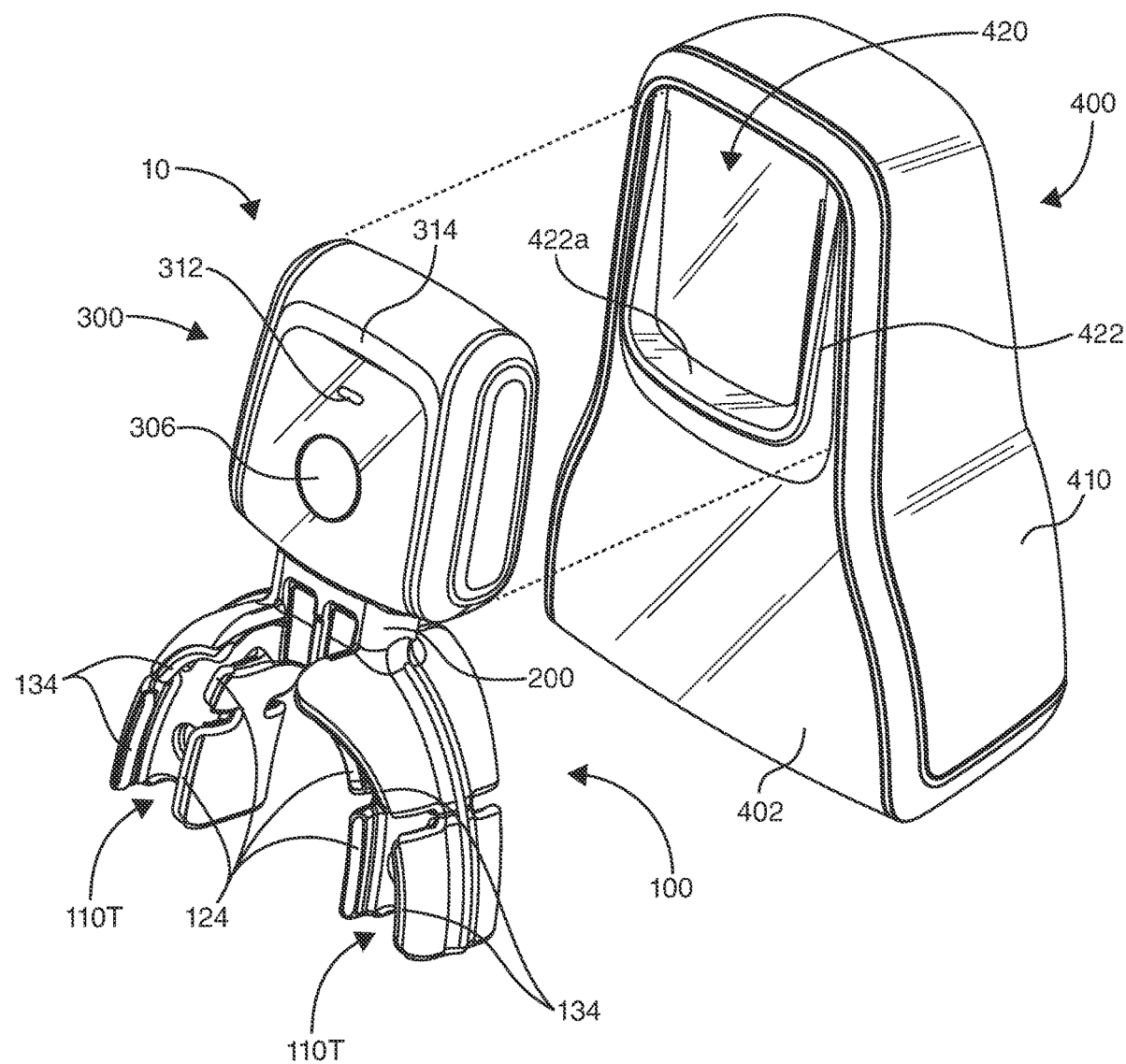
FIG. 1 is a perspective view of an intraoral electrical stimulation apparatus and associated storage and/or charging stand according to the present invention.
Figure 2:
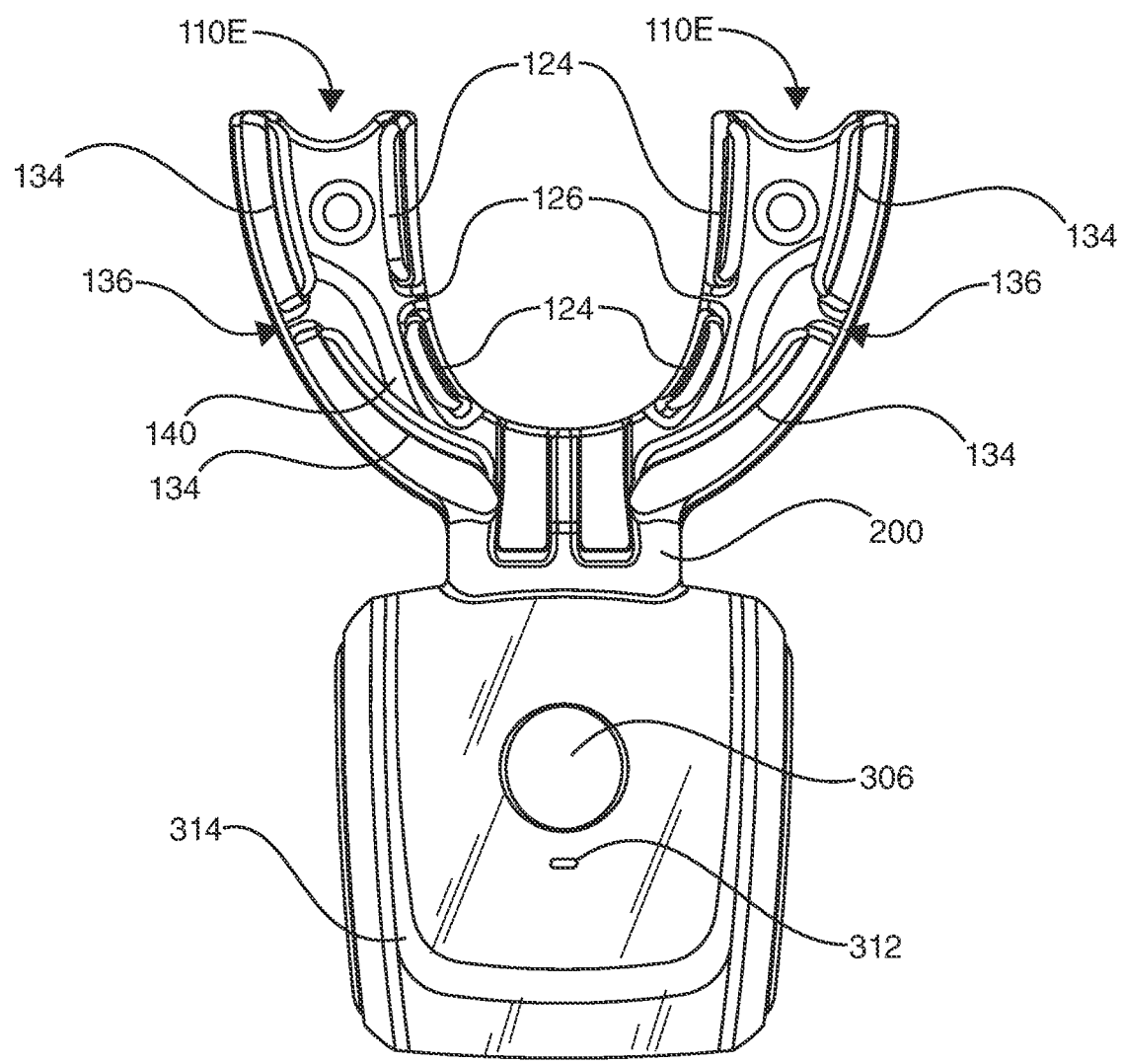
FIG. 2 is a top plan view of a mouthpiece and controller according to the present invention.
Figure 3:
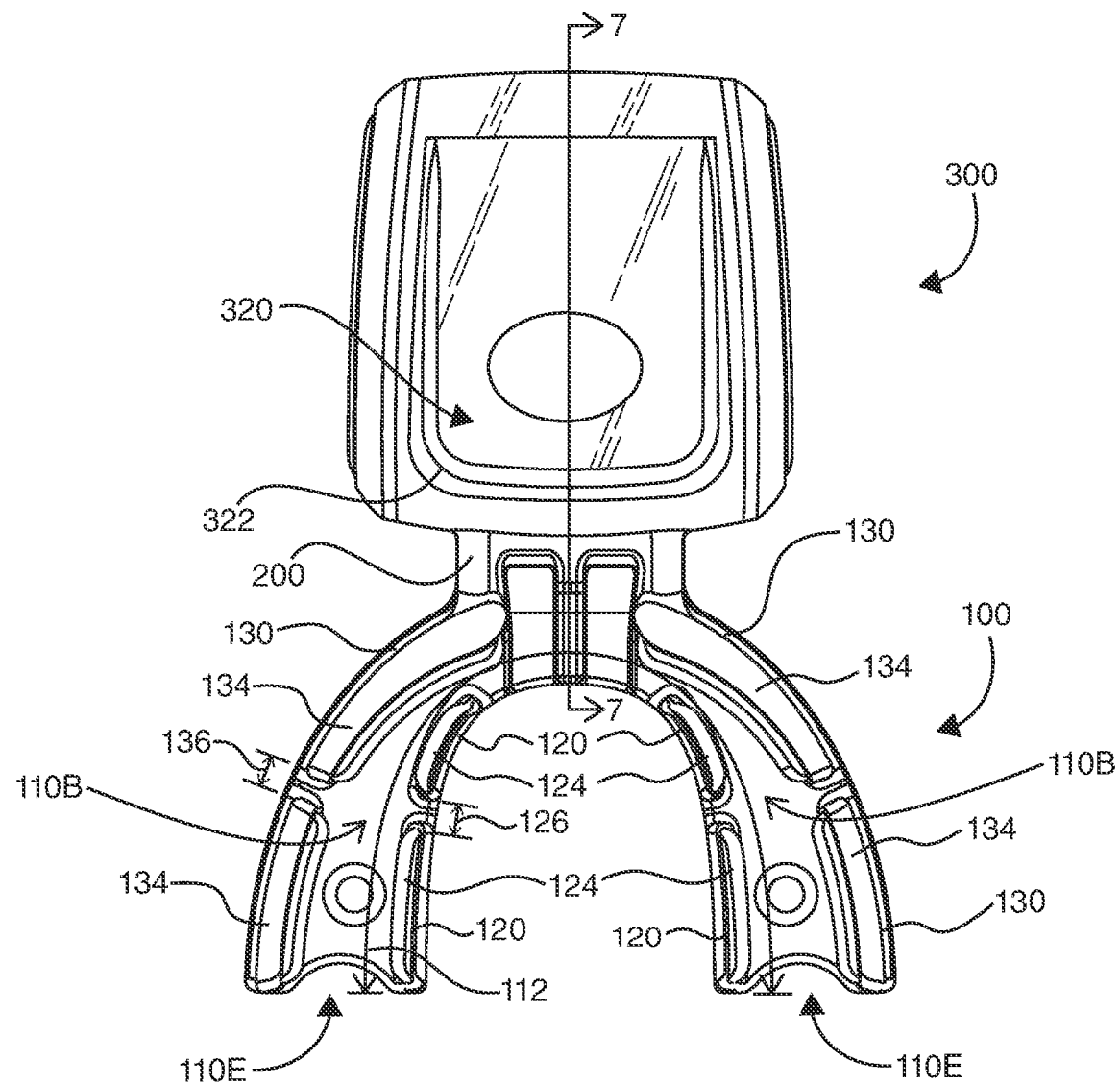
FIG. 3 is a bottom plan view of a mouthpiece and controller according to the present invention.
Figure 4:
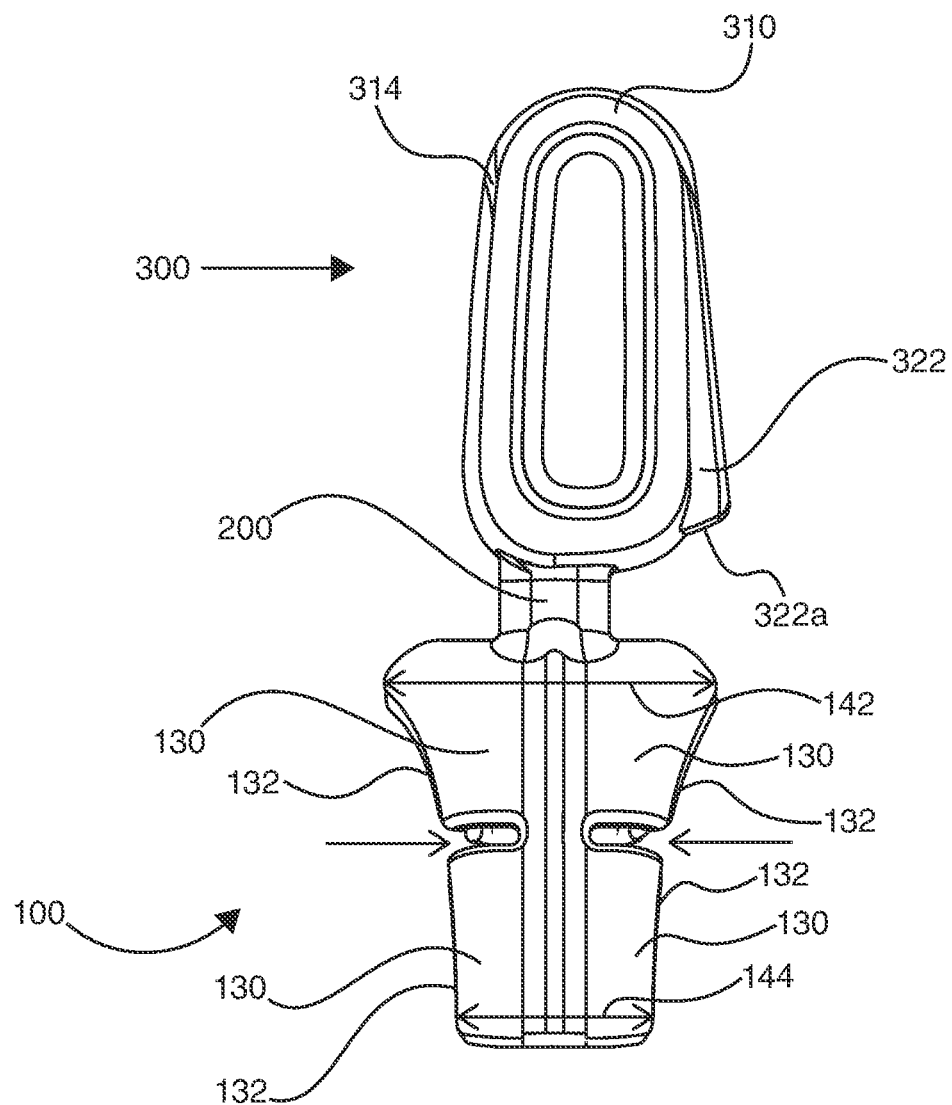
FIG. 4 is a left side elevation view of a mouthpiece and controller according to the present invention.
Figure 5:
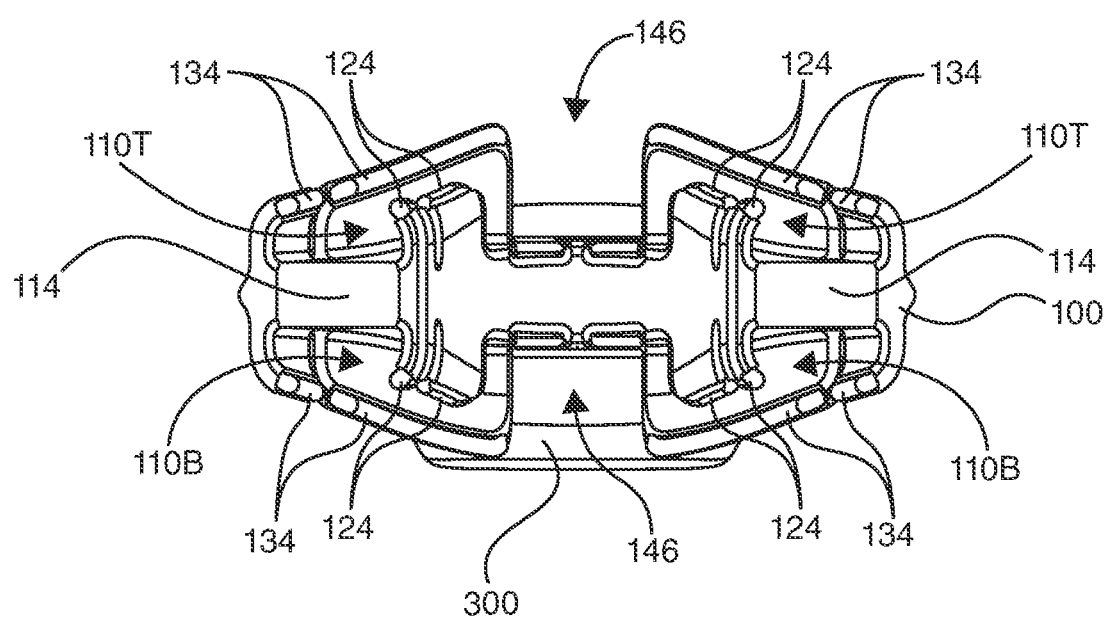
FIG. 5 is a rear elevation view of a mouthpiece and controller according to the present invention.

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention.

It is known in the art that oral bacteria cannot survive when exposed to low-microampere direct current electricity. This method of killing oral bacteria and treating bacteria-caused conditions such as gingivitis has been demonstrated in Nachman, U.S. Pat. No. 4,244,373 of Jan. 13, 1981 and in Detsch, U.S. Pat. No. 4,509,519 of Apr. 9, 1985. Killing oral bacteria has the added benefit of preventing tooth decay and dental caries, or cavities. Generally, tooth decay is attributed to aerobic acid-producing bacteria whose acid causes uncompensated demineralization of the teeth. However, Nachman does not instruct optimal approaches to reducing oral bacteria including aerobic and anaerobic bacteria on a species-by-species level and instead teaches a generic, untargeted treatment.

While researching the effect of direct current electricity on the mouth, the applicants discovered that by increasing the current level to the approximate range of 50 to 250 microamperes ($\mu A$), a direct current electrical stimulation was able to deliver new and unexpected therapeutic, prophylactic, cosmetic, and regenerative benefits previously unknown in the art.

Specifically, by utilizing a direct current in the aforementioned range, not only did such a stimulation kill bacteria, but it was also found to kill or disable viruses and fungus as well. Studies from the podiatric field have shown that higher current levels than those used in existing oral electrical stimulations are necessary to effectively treat fungal infections ("Low-Voltage Direct Current as a Fungicidal Agent for Treating Onychomycosis", Kalinowski, et al., Journal of the American Podiatric Medical Association Vol. 94 No. 6: 565-572, 2004). By applying this knowledge of increased current levels from research outside the art, the applicants were able to add fungicidal and viricidal benefits to a method already known to be bactericidal. The applicants' studies have shown that these microbicidal properties begin to take effect within approximately 5 and 15 minutes of stimulation, reducing both supra- and sub-gingival microbes.

In addition, the applicants' clinical research unexpectedly demonstrated that a direct current in the approximate range of 50 to 250 microamperes was able to regenerate gingival tissues, providing a non-surgical alternative for those with recessed gums. While the osteogenic properties of electricity have been known in the art, the connection between non-osseous tissue regeneration and electricity were not well known in the art prior to these experiments. The unique current range associated with the method and apparatus of this invention is one of a few effective methods in the dental field to accomplish effective gingival tissue regeneration in a non-surgical manner.

In further research, the applicants conducted preclinical testing that examined the effects of direct current stimulation on three different oral bacteria (*F. nucleatum, S. oralis, P. gingivalis*) in both saline and saliva solutions. This testing varied the current levels, inoculum size of bacteria, solution medium, and stimulation time to develop an optimal reduction in these three bacteria species associated with both periodontal and systemic diseases.

The results of this testing yielded unexpected results and showed that each different bacterium had a different dose response to DC stimulation. Through this testing, the applicants identified stimulation parameters that were able to kill up to 100% of *S. oralis*, 99.1% of *F. nucleatum*, and 52.3% of *P. gingivalis* in a single stimulation session lasting thirty minutes or less. This research yielded specifications for DC-based stimulations of targeted pathogens that was previously unknown in the art. The optimal stimulation parameters discovered in this research and described in this method can provide an innovative way to reduce these three species of bacteria, in both supra- and sub-gingival environments, and thus prevent and/or treat their associated complications including periodontal disease, biofilm formation, as well as the systemic diseases correlated to these oral pathogens.

In addition, scanning electron microscopy (SEM) was conducted on *F. nucleatum* colonies before and after a 30 minute stimulation, according to the method of this invention, to better understand the mechanism by which the method according to this invention is able to reduce bacterial levels. The SEM imagery suggested that the method according to this invention interferes with bacterial cellular division and can weaken the outer envelope (cell membrane) resulting in fragile cellular structures that can easily break. It is contemplated that this phenomenon is an example of electroporation, where the permeability of cellular membranes may be affected by electrical stimulation either temporarily or permanently. It is further contemplated that the electroporation caused by the method according to this invention could play a role in developing new therapies in molecular biology which would take advantage of this cellular permeability and introduce new material into the cells of oral pathogens or oral tissues through mechanisms including, but not limited to, genetic material (transfection) such as DNA, RNA, sRNA, siRNA, plasmids, etc. These effects would prove a new tool in targeted gene therapies for oral applications.

Specifically, the method according to the present invention has been shown to reduce viable colony forming units (CFU) in various oral bacteria.

Table 1 below shows the efficacy of stimulation according to the present invention at current levels of 50 μA or 500 μA for 5-, 10-, 20-, and 30-minute durations for bacterial cultures ranging from $10^4$ to $10^7$ colony forming units (CFU) of *Streptococcus oralis* in a saline solution.

TABLE 1

In Vitro Efficacy Against

| CFU | μA | 0 Min | 5 Min | 10 Min | 20 Min | 30 Min |
|---|---|---|---|---|---|---|
| 10e4 | 50 μA | 1120 | 1080 | 600 | 320 | 280 |
| | 500 μA | 1120 | 1200 | 800 | 240 | 0 |
| 10e5 | 50 μA | 10000 | 9600 | 8400 | 9200 | 7600 |
| | 500 μA | 11600 | 10400 | 11200 | 10800 | 8400 |
| 10e6 | 50 μA | 80000 | 63200 | 52800 | 32400 | 24800 |
| | 500 μA | 80800 | 70000 | 15200 | 14000 | 15600 |
| 10e7 | 50 μA | 1280000 | 1080000 | 1040000 | 800000 | 440000 |
| | 500 μA | 1080000 | 520000 | 160000 | 120000 | 320000 |

Table 2 below shows the efficacy of stimulation according to the present invention at current levels of 50 μA or 500 μA for 5-, 10-, 20-, and 30-minute durations for bacterial cultures ranging from $10^4$ to $10^7$ CFU of *Streptococcus oralis* in a saliva solution.

TABLE 2

In Vitro Efficacy Against
*Streptococcus oralis* in Saliva

| CFU | μA | 0 Min | 5 Min | 10 Min | 20 Min | 30 Min |
|---|---|---|---|---|---|---|
| 10e4 | 50 μA | 160 | 160 | 80 | 80 | 40 |
| | 500 μA | 200 | 80 | 80 | 80 | 80 |
| 10e5 | 50 μA | 5600 | 5600 | 6800 | 5600 | 4000 |
| | 500 μA | 8400 | 6800 | 7200 | 6400 | 2800 |
| 10e6 | 50 μA | 25600 | 25200 | 15200 | 17200 | 18400 |
| | 500 μA | 23600 | 16800 | 15600 | 17600 | 15200 |
| 10e7 | 50 μA | 316000 | 284000 | 300000 | 276000 | 220000 |
| | 500 μA | 324000 | 328000 | 300000 | 292000 | 252000 |

Table 3 below shows the efficacy of stimulation according to the present invention at current levels of 50 μA or 500 μA for 5-, 10-, 20-, and 30-minute durations for bacterial cultures ranging for $10^4$ and $10^6$ CFU of *Fusobacterium nucleatum* in a saline solution.

TABLE 3

In Vitro Efficacy of Device Against
*Fusobacterium nucleatum* in Saline

| CFU | μA | 0 Min | 5 Min | 10 Min | 20 Min | 30 Min |
|---|---|---|---|---|---|---|
| 10e4 | 50 μA | 480 | 280 | 280 | 120 | 40 |
| | 500 μA | 560 | 440 | 400 | 200 | 120 |
| 10e6 | 50 μA | 94000 | 91600 | 85600 | 70400 | 84400 |
| | 500 μA | 46400 | 45600 | 27200 | 2000 | 400 |

Table 4 below shows the efficacy of stimulation according to the present invention at current levels of 50 μA or 500 μA for 5-, 10-, 20-, and 30-minute durations for bacterial cultures ranging from $10^4$ to $10^6$ CFU of *Fusobacterium nucleatum* in saliva.

TABLE 4

In Vitro Efficacy of Device Against
*Fusobacterium nucleatum* in Saliva

| CFU | μA | 0 Min | 5 Min | 10 Min | 20 Min | 30 Min |
|---|---|---|---|---|---|---|
| 10e4 | 50 μA | 1480 | 1480 | 1560 | 680 | 880 |
| | 500 μA | 2360 | 2360 | 1720 | 1240 | 1080 |
| 10e5 | 50 μA | 19600 | 19600 | 15200 | 14400 | 14000 |
| | 500 μA | 18000 | 17200 | 14400 | 11200 | 10800 |
| 10e6 | 50 μA | 348000 | 112000 | 120000 | 72000 | 68000 |
| | 500 μA | 156000 | 128000 | 124000 | 32000 | 28000 |

Table 5 below shows the efficacy of stimulation to the present invention at current levels of 50 μA or 500 μA for 5-, 10-, 20-, and 30-minute durations for bacterial cultures ranging for $10^5$ CFU of *Porphyromonas gingivalis* in a saline solution.

TABLE 5

In Vitro Efficacy of Device Against
*Porphyromonas gingivalis* in Saline

| CFU | μA | 0 Min | 5 Min | 10 Min | 20 Min | 30 Min |
|---|---|---|---|---|---|---|
| 10e4 | 50 μA | 3440 | 2040 | 2720 | 1640 | 1640 |
| | 500 μA | 2440 | 2120 | 2200 | 1880 | 1840 |

Thus, this method and corresponding apparatus are able to achieve multiple prophylactic, therapeutic, cosmetic, and regenerative effects whose combination was not previously known or available in the art. Namely, these effects are: promotion of oral osteogenesis, destruction or disabling of oral microbes, gingival tissue regeneration, reduction and prevention of the formation of oral biofilms, caries prevention, increased oral vasodilation and oral blood flow, treatment of common oral conditions such as gingivitis and periodontitis, treatment of systemic diseases and conditions correlated with oral pathogens, and generally improved oral hygiene.

Turning now to the figures, FIG. 1 shows one embodiment of a stimulation apparatus 10 according to this invention. The stimulation apparatus 10 is preferably a stand-alone device comprising a mouthpiece 100 and a controller 300 which may be physically supported by and operatively charged by a charging station or stand 400. Generally, the mouthpiece 100 is sized and configured to be received in a human mouth while positioning one or more electrodes at a desired location within the mouth. With reference also to FIGS. 2-5, the mouthpiece 100 includes at least one substantially U-shaped channel 110 configured to receive any maxillary or mandibular teeth of a human, and preferably includes a top U-shaped channel 110T and an opposing bottom U-shaped channel 110B, the channels 110 configured to preferably contemporaneously receive any maxillary teeth and any mandibular teeth of the same human. The two U-shaped channels 110 are preferably separated from each other along at least a majority of their length 112 by a channel base 114. Forming the channels 110 in connection with the channel base 114 are opposing lingual 120 and buccal 130 sidewalls, extending preferably substantially perpendicular from the channel base 114. The lingual sidewalls 120 terminate in a lingual free edge 122, along a majority of which (and preferably along the entire lingual free edge 122) is provided one or more lingual electrodes 124. The lingual electrodes 124 are preferably formed from an electrically conductive silicone, and may be separated by one or more insulative gaps, such as a lingual wall air gap or notch 126 or other electrically insulative material. The buccal sidewalls 130 terminate in a buccal free edge 132, along a majority of which (and preferably along the entire buccal free edge 132) is provided one or more buccal electrodes 134. The buccal electrodes 134 are preferably formed from an electrically conductive silicone, and may be separated by one or more insulative gaps, such as a buccal wall air gap or notch 136 or other electrically insulative material, such as electrically insulative silicone. The mouthpiece 100 is preferably formed (e.g., molded) from tissue facing materials that are relatively comfortable, such as materials having a Shore A hardness of less than or equal to 80.

The connections made between the electrodes 124,134 and the circuitry in the controller 300 is made through a neck portion 200. The connection from electrodes 124,134 to the neck portion 200 may be achieved using flexible circuit technology, such as copper-clad polyimide, but a multi-shot injection mold including a first electrically insulative material and a second electrically conductive material to form electrical traces 140 may be more preferred. That is, a first mold may be used to form electrically conductive silicone into a desired pattern, extending from a first connector end to and including one or more electrodes 124,134 to make an electrically conductive skeleton. The electrically conductive skeleton may then be overmolded with electrically insulative silicone, so as to form a majority of the mouthpiece 100 and insulating the electrically conductive traces 140 that form the skeleton from each other. After insulation, the exposed electrically conductive areas are the electrodes 124,134, and a terminal surface within the neck portion 200.

The electrical traces 140 within the mouthpiece 100 are then electrically coupled to a header connector 210 mounted or to be mounted within the controller housing 310, which is further described below. Specifically, the header connector includes pins 212, each pin preferably associated with and physically inserted into an electrically conductive silicone path (140 in FIG. 7) to an electrode 124 or 134. The maximum resistance of any conductive path from a terminal surface 142 of the trace 140 in the neck portion 200 to any portion of any respective electrode 124,134 is preferably less than 25 kΩ.

Figure 7:
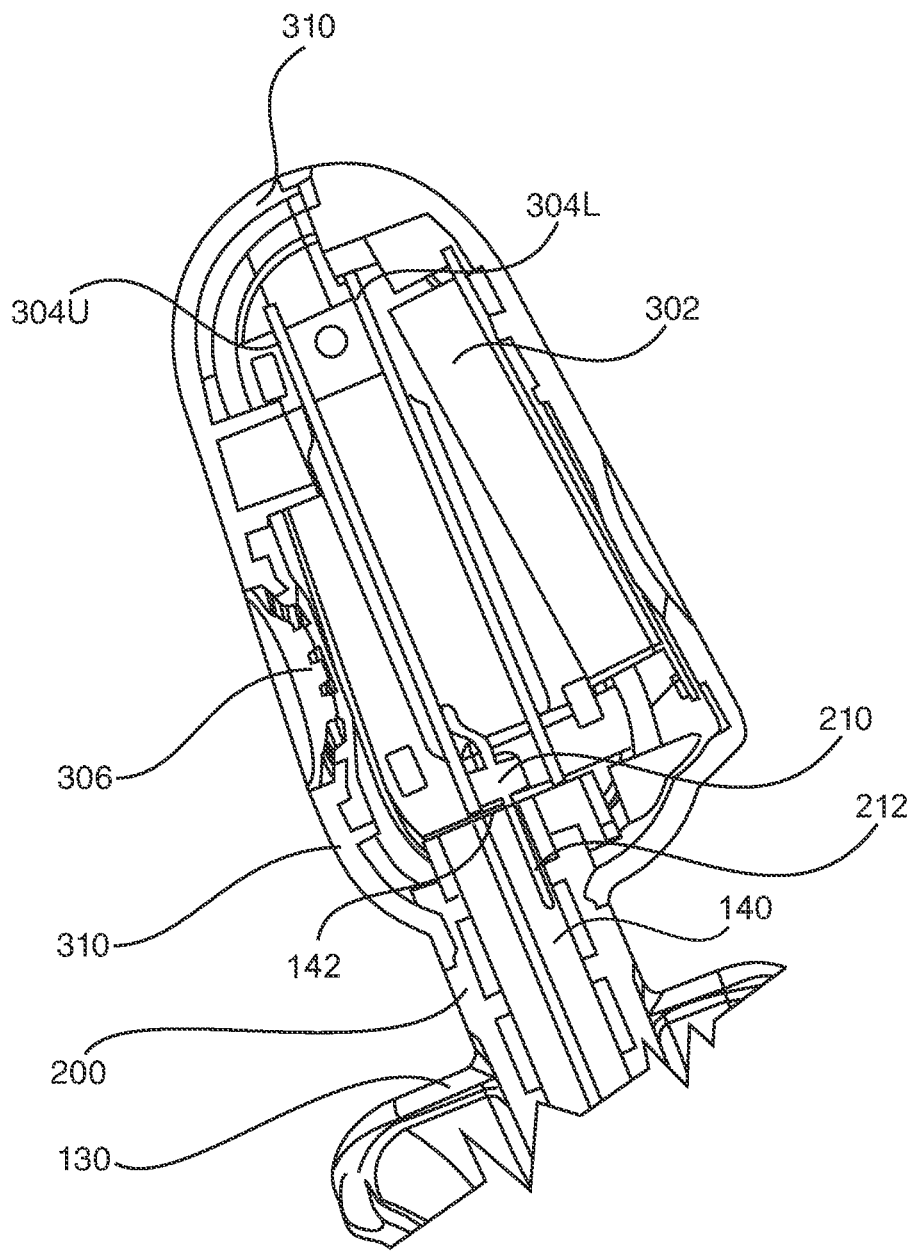
FIG. 7 is a partial cross-section view of an embodiment of a controller according to the present invention, taken along lines 7-7 in FIG. 3.
Figure 8A:
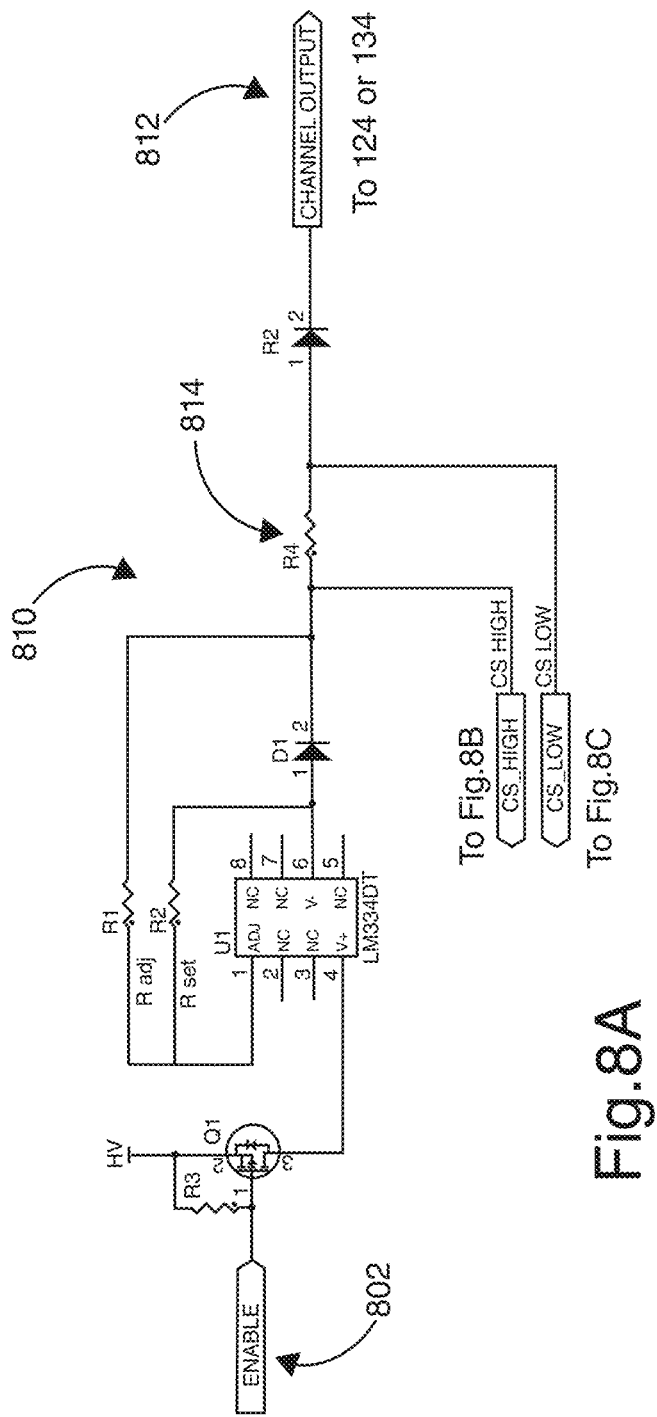
FIG. 8 includes schematic views of portions of an electrical circuit in an embodiment of a controller according to the present invention.
Figure 8B:
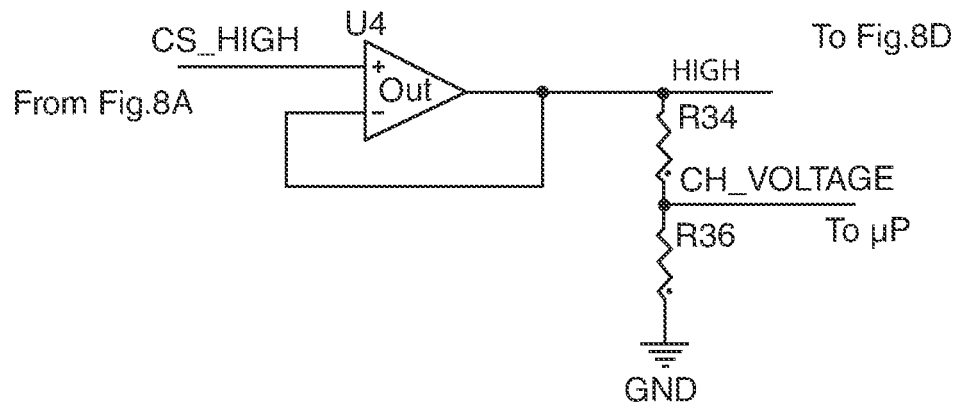
Figure 8C:
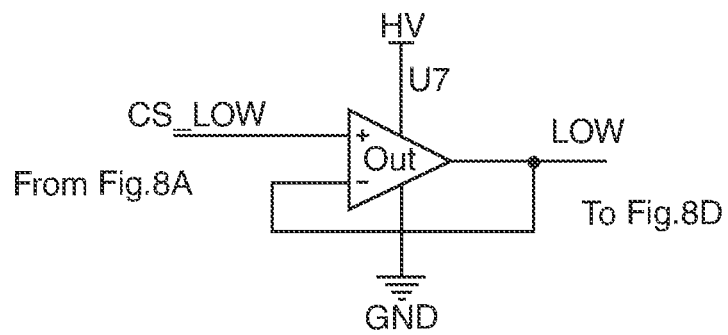
Figure 8D:
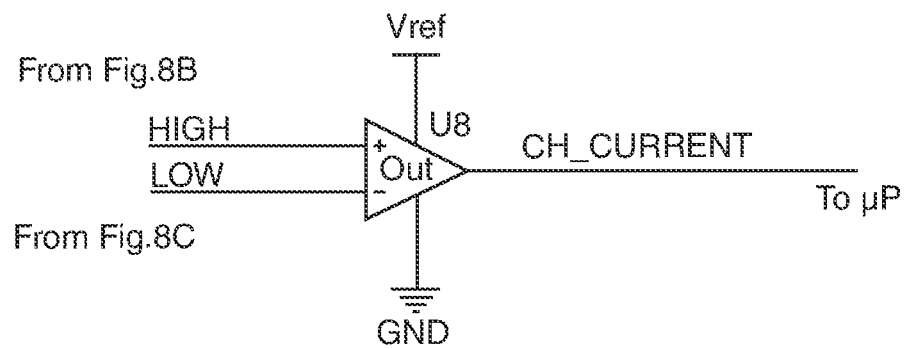
Figure 9:
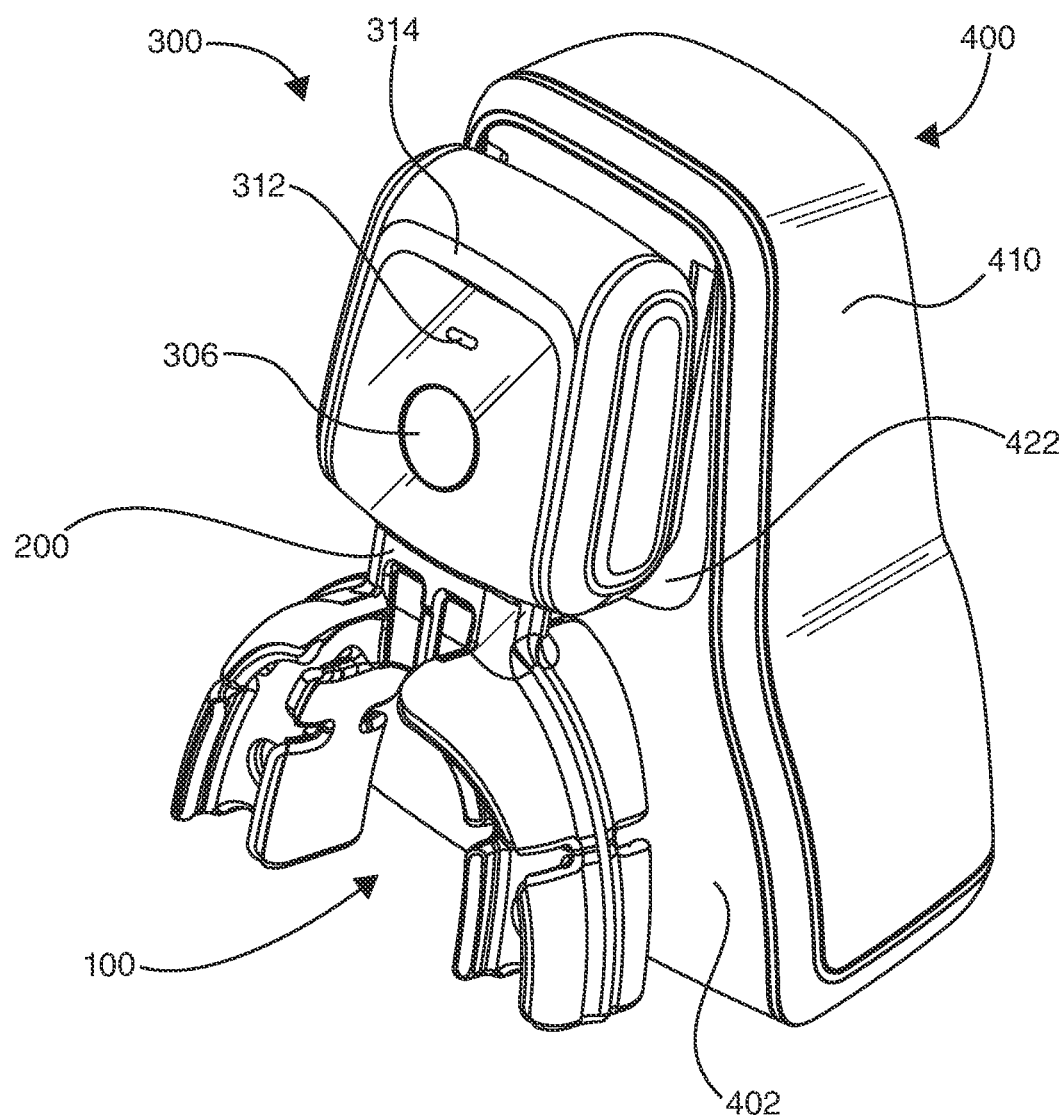
FIG. 9 is a front perspective view of the embodiment of FIG. 1, showing the mouthpiece/controller supported by the stand.

With reference also to FIG. 7, the controller 300 preferably comprises a housing 310 configured to be secured to the mouthpiece 100. The housing 310 contains a battery 302 and electronic circuitry to generally control the timing of connection (i.e., switching) of the electrodes 124,134 to deliver charge from the battery 302. The battery 302 is preferably a rechargeable lithium ion battery with a fully-charged capacity capable of performing at least seven consecutive stimulation sessions, where such session durations are 20 minutes in length. The battery 302 is preferably rechargeable from a fully depleted state in less than 12 hours. The battery 302 is preferably rated for at least two hundred (200) charge/discharge cycles. While the circuitry may be operatively mounted to one or more printed circuit boards 304, two circuit boards (a lower board 304L and an upper board 304U) are preferred to provide an improved packaging footprint. The housing 310 may comprise a single or several housing pieces (e.g., housing top, bottom, sides, etc.) such as a molded polycarbonate plastic, a polycarbonate/ABS alloy (PC/ABS), which is preferably biocompatible. Regardless of the materials used to construct the mouthpiece 100 and the controller 300, the apparatus 10 preferably is capable of withstanding a gravitational drop (~9.81 m/s$^2$) onto a relatively hard surface (e.g., stone or ceramic tile, vinyl overlaid on wood substrate, or concrete) from a distance of about two meters (2 m).

Figure 6:
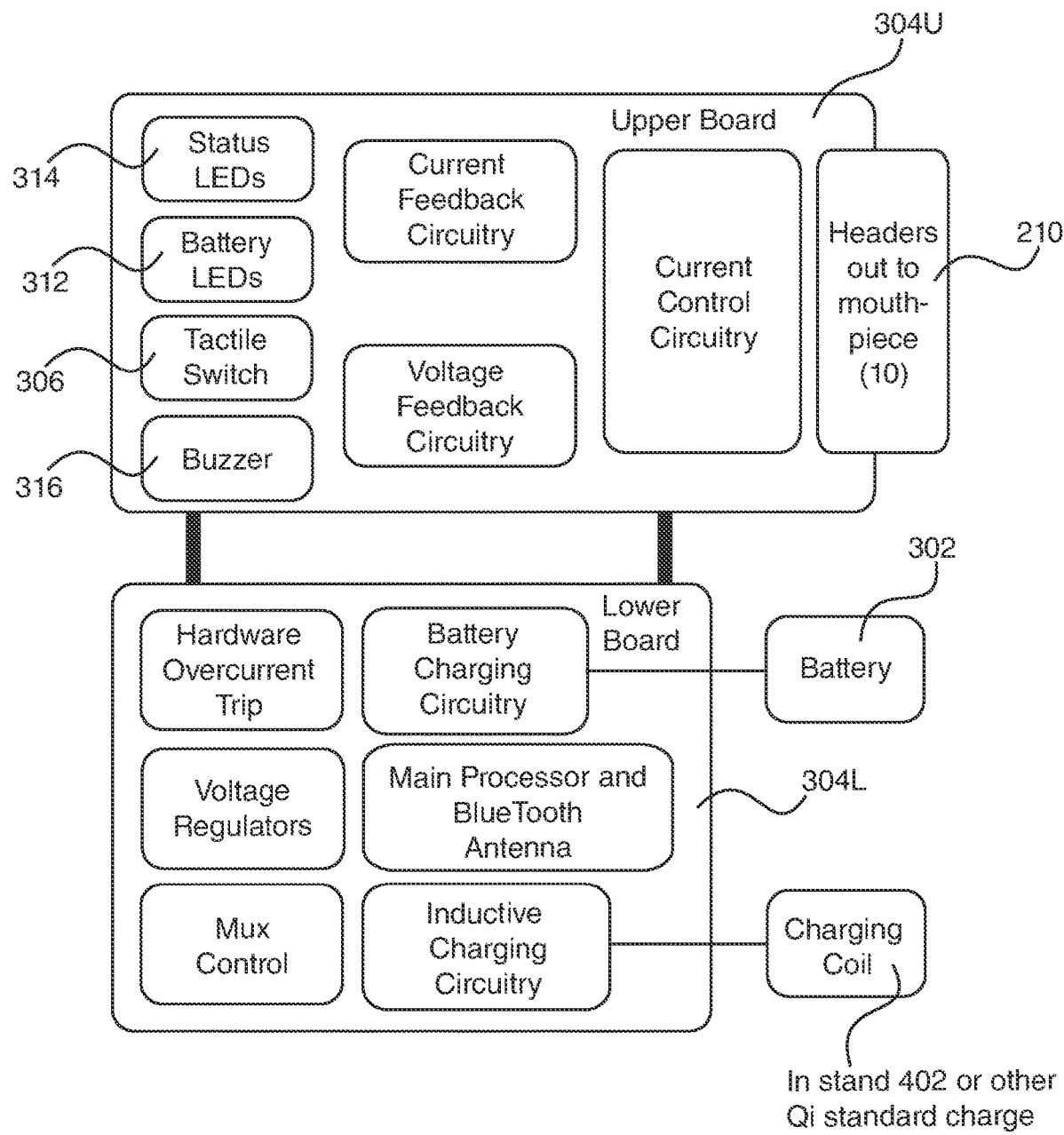
FIG. 6 is a diagrammatic representation of an electrical circuit of a controller according to the present invention.

FIG. 6 generally provides a diagram of the functional blocks of circuitry contained in the housing 310, including a programmable microprocessor (preferably in conjunction with a communications antenna), inductive charging circuitry to receive wireless inductive charging for the battery 302, hardware overcurrent protection, current and voltage feedback for monitoring delivery parameters and open circuit conditions, and user interface components.

The controller 300 preferably provides a user input interface in the form of a single pushbutton 306 (preferably debounced in hardware or software) and a user output or feedback interface, preferably including one or more of a battery indicator light 312, a status (or stimulation or treatment indicator) light 314, and an audible buzzer or speaker 316. The pushbutton 306 state (activated/deactivated) is monitored to control functionality. The battery indicator light 312 preferably is capable of displaying a plurality of colors (e.g., white and amber) preferably in either a consistently lit condition, flashing condition (which may be at different rates), or alternating colors, depending on the feedback to be provided. The treatment indicator 314 preferably is capable of displaying a plurality of colors (e.g., red, white and blue) preferably in either a consistently lit condition or flashing condition (which may be at different rates), or alternating colors, depending on the feedback to be provided. User feedback may additionally or alternatively be provided by touch, through the use of a haptic feedback generator, such as a vibratory motor. Preferred feedback is as shown in the table provided in FIG. 11. Notes related to FIG. 11 (indicated by superscript in the table, are as follows:

1. If the device has transitioned to LOW BATTERY from the COMPLETE state, the treatment LED 314 will continue Flashing-White and audible feedback will be Off.

2. Flashing-White when battery is charging, On-White when charging is complete.

3. If the device is placed on the charging stand while in the FAULT state, the device will continue to display the Flashing-Red treatment indicator light 314. The device will display the battery indicator light 312 according to the current battery charge (Flashing-White/On-White), but will not provide audible feedback when placed on the charger to avoid this being misinterpreted as clearing the fault.

4. The battery indicator light 312 will turn off if the device 10 is left on the charger 400 for greater than 10 minutes after charging is complete. The charger 400 will continue to charge during this time period if the battery voltage drops below the charging threshold, but the battery indicator 312 will remain off.

Generally, the electrical circuitry can be described as having multiple channels controlled and monitored by a microprocessor, where each channel is associated with the operation of one or more electrodes 124,134. The channels may be enabled or disabled independently of other channels, although each channel may control multiple electrodes. Additionally or alternatively, one or more electrodes may be permanently specified and operated as only a return electrode. A preferred embodiment includes eight channels, each capable of driving 125 µA of direct electrical current across a resistance of up to 50 kΩ.

As can be seen in FIGS. 8A-8D, for each electrode channel, an enable signal 802 is received by a channel drive circuit 810. When activated, the enable signal 802 flips a switch (a MOSFET in this example) to provide voltage to a current source regulator, which then provides electrical current to the channel output 812. A sense resister 814 is used to determine whether or not current is flowing and preferably how much current is flowing. CS_HIGH and CS_LOW signals are run through a comparative circuit to activate the CH_CURRENT signal to indicate that current is flowing. CH_VOLTAGE may be monitored to determine voltage and current levels delivered to a respective channel.

The operation of the controller 300 by a user (not shown) is preferably performed through the pressing of the push button 306. For example, the user can start or pause the delivery of current to the mouthpiece 100 by pressing the push button 306. To prevent unintentional operation, the duration of the pressing of the push button 306 is sensed and debounced.

The controller 300 is preferably configured by a clinician or other trained staff member prior to a user interfacing with the stimulation apparatus 10. Additionally, or alternatively, the patient may configure the controller 300. Preferably configuration of the controller 300 is performed through attachment of an additional piece of hardware (not shown) connected to the controller 300, but may also take place through a wireless connection (e.g. Bluetooth®, Wi-Fi, near field communications (NFC), infrared, magnetic). Finally, the controller 300 may be provided with a default stimulation regimen to reduce or eliminate initial configuration effort by a clinician or patient.

Configuration parameters preferably include: selection of electrode configurations to provide direct current for stimulation; selection of direct current output values, for example, 6 µA, 12 µA, 18 µA, 25 µA, 50 µA, 62 µA, 75 µA, 100 µA, 125 µA, 150 µA, and 200 µA (preferably not to exceed 1,000 µA total current across all delivery electrodes at any one time); and selection of stimulation session duration (preferably from 1 minute through 30 minutes selectable in increments of 1 minute). Exemplary preferred configuration parameters can be seen in the table provided in FIGS. 12A and 12B.

The controller 300 is preferably capable of monitoring compliance of protocols and stimulation sessions performed by the stimulation apparatus 10 and recording a number of performance metrics in non-volatile memory (e.g., FLASH memory), such as counts of predetermined and monitored events and/or data associated with such events. The records may be utilized by a clinician (not shown) to evaluate and discuss stimulation response and efficacy. The controller 300 may also be configured to dynamically monitor the electrical characteristics (i.e., resistance, voltage, current) and adjust stimulation parameters or settings without clinician or user intervention. A real-time clock is preferably used and referenced to record the time and date at which the metrics and data are collected. Separate and apart from the real-time clock (which may be seeded by a wireless communication device or network), a real-time counter is maintained to track timing for automatic state changes and to track run time (up time).

For example, counters may be establish to track the number of times a particular event occurs. Counters may be maintained in nonvolatile memory, such as those preferred counters shown in the table in FIG. 13A and FIG. 13B. Some metrics and data collected may include the following (along with the dates and times of such occurrences): the number of stimulation sessions (e.g., treatments) started; the number of successfully completed stimulation sessions (e.g., treatments); the number of open circuit faults; the number of stimulation sessions (e.g., treatments) with an open circuit; the number of stimulation sessions (e.g., treatments) with an open circuit that still completed successfully; the number of overcurrent faults; the number of low battery faults; the number of times the device was paused; the number of stimulation sessions (e.g., treatments) that were paused but still completed successfully; the number of times the user turns the device on; the number of times the device is powered off by the user; the number of times the device is powered off by software; and the total number of minutes the device has run since a memory reset. Recorded metrics and data may be stored only in non-volatile memory within the controller 300 and accessed through a physical connection (e.g., a serial UART connection if the housing 310 is removed, or through a serial connector provided through the housing 310). Additionally or alternatively, recorded metrics and data may be accessed over a wireless connection (e.g. through a software application on a BLE-enabled wireless communication device) or even automatically pushed to a wireless communication device over a wireless network to then be stored on the wireless communication device or remotely therefrom, such as on a remote data storage device networked with the wireless communication device (cloud storage or remote server, which may be associated with the manufacturer and/or seller of the apparatus 10, a care provider (e.g., dentist, hygienist, administrative staff), an insurance company, or the user (or user's guardian).

The automatic data push could also be based on a time interval or an event occurrence, such as transition from OFF to READY, entering the CHARGING state, entering the OFF state, etc. Pushed data may include user stimulation session data (e.g., patient compliance metrics), firmware version, device errors, and/or physical location of the apparatus 10 and/or charger 400 (if GPS or network location functionality provided).

The particular technology utilized for such data pushing may be assembled from generally known hardware technologies, heretofore not known to be used in conjunction with any oral appliances. The data push from the controller 300 may be directly to the charger 400 as an intermediary for forwarding over a wireless communication network (e.g., WAN, LAN, etc.), such as WiFi/LoRa/LoRaWAN/Helium or even a low-power wide-area network or mesh network.

Not only may a count of a particular event be maintained, but data associated with a particular event occurrence may also be logged. Types of events to be recorded in an event log for the controller may also be stored in nonvolatile memory, including those shown in the table in FIG. 14.

Preferably, the events log can store a minimum of 2,000 events. If the nonvolatile memory allocated to the events log is exceeded, then oldest events will be overwritten to store new data.

The nonvolatile memory will preferably store at least the following occurrences and related information: how many minutes of stimulation (up to 30 minutes) the user completed; whether the mouthpiece was disconnected while running (e.g., OPEN state occurrence); whether an overcurrent fault occurred; total charge delivered per channel for a particular stimulation duration (e.g., treatment), in units of coulombs (C) or microcoulombs (µC); and whether a low battery fault occurred.

The controller 300 may also be configured to detect when, the mouthpiece 100 is not located in the mouth of a user during a stimulation session, as discussed in connection with FIG. 8. To do so, the controller 300 monitors the delivery of current and whether current is detected on any of the plurality of cathodic electrodes. If no current is detected, the controller 300 may pause stimulation and indicate a fault condition. For instance, the controller 300 monitors the stimulation circuits, including the anodic and cathodic electrodes. The controller 300 includes circuitry to measure or predict the amount of current to be delivered to the mouthpiece 100 (delivered current), and may also measure the amount of return current received from the mouthpiece 100 (return current). The circuitry then compares the return current to the delivery current, and if the difference is greater than a predetermined value (e.g., a percentage of the delivered current, such as 10% to about 50%), then stimulation is paused, preferably on all electrodes, and a fault message is displayed on the controller. Once the difference between delivered current and return current is less than the predetermined amount, then the stimulation program or regimen will resume from where it left off, preferably so no or little stimulation time is lost.

Figure 17:
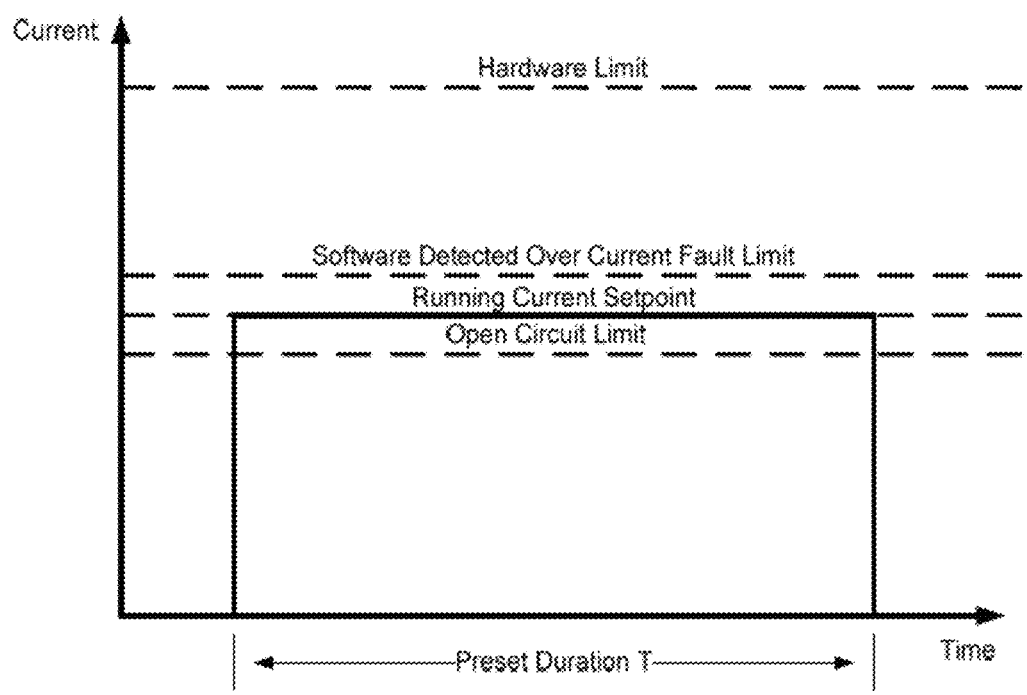
FIG. 17 is a graph providing current delivery monitoring parameters according to the present invention.

FIG. 17 provides parameters for monitoring the current delivered to a delivery electrode. As described above, the running current setpoint and also the duration "T" is determined and set during configuration prior to a patient using the stimulation apparatus 10, with the recommended setting for duration "T" at two seconds. The open circuit is preferably approximately 80% of the running current set point and the over current fault limit is preferably 120% of the running current set point. The hardware limit is preferably approximately 200 to 300 µA per stimulation channel (e.g., per anodic electrode).

The current is preferably polled eight times per second when the controller 300 is delivering current to any delivery electrode.

If the current detected is less than the open circuit limit for more than a preset duration, stimulation will pause and a notification will be indicated. If the current detected is more than an over current fault limit for more than the preset duration, stimulation will be stopped and a fault notification will be indicated.

It is further contemplated that the stimulation apparatus 10 be fully compatible with wireless technology such as Bluetooth® technology, near-field communication, and wi-fi to communicate with a user's electronic device (not shown), such as a cell phone, tablet, or personal computer. Preferably, a user may review usage history, the prescribed stimulation plan, and/or a comparison of usage history versus stimulation plan. The stimulation apparatus 10 may also provide notifications regarding scheduled stimulation sessions to any of the user's electronic devices. This functionality is contemplated as operating through an application (not shown) downloadable to a user's electronic device. The application may also be configured to share this data with a central server for storage, remote monitoring by the prescribing clinician, provide one-way or two-way communication between patient and clinician, and/or allow for a clinician to remotely adjust the stimulation parameters. Additionally, firmware upgrades may be supplied to the controller 300 wirelessly.

The controller 300 preferably includes wireless communication technology, such as a Bluetooth Low Energy (BLE) module, which may be incorporated into the microprocessor packaging. When the controller 300 is powered on (i.e., not in the OFF state), the controller preferably periodically transmits BLE advertisement packets, which preferably includes a device identifier such as a Unique Device Identifier (UDI) as may be assigned by a regulatory authority, such as the U.S. FDA. The BLE communication channel is preferably used to transmit information about or contained in the controller 300, such as software version, programmable parameters, event log data, counter data, and/or software state (e.g., READY, RUN, OPEN, etc.) and/or changes (since last transmission) in any of the foregoing. The BLE interface may also be used to exchange information with a software application (such as a user or physician service application) on a remote wireless communication device, such as a tablet computer, mobile phone, or other BLE enabled device, which preferably also includes a real-time clock. The real-time clock data may be received from the application by the controller 300 and stored and referenced to start, maintain, and/or update its own real-time clock.

Specifically, an application (running on a wireless communication device) may scan (on demand or periodically) for BLE advertisement packets transmitted by the controller 300. By manipulating a user interface on the device, the user may then pair the device to the stimulation apparatus 10 by selecting from a list of nearby advertising BLE enabled devices. Additionally, or alternatively, the application is preferably capable of pairing the wireless device to the stimulation apparatus 10 via RSSI (Received Signal Strength Indicator), where the wireless device need only be brought into a predetermined proximity of the apparatus 10 to pair. The user may manipulate the user interface of the application to engage or disengage the RSSI function.

Once the mobile device is paired to the apparatus 10, the present date and time (from a local time stored on the mobile device or from a network, such as wifi or cellular) is preferably transmitted to the apparatus 10 to store in the event log. The application may confirm this connection and transmittance by displaying the contents of the event log for the user to see. Further, the application may display parameter values and counters of the paired apparatus 10. Preferably, the application offers the option to highlight and notify the user to changes in the event log, parameter values, or counter values as they occur (or soon after) on the apparatus 10, to provide a real-time update.

The application may also preferably display the current software state of the apparatus 10 and information related to that state. For example, when the apparatus 10 is in the RUN or OPEN states (i.e. when stimulation is in progress or paused, respectively), the application may display a timer counting down the time remaining in the stimulation cycle as well as an electrical current and voltage measurement for each channel on the apparatus 10. While in these states, the application also preferably provides the option to save, from the apparatus 10, the event log, parameter values and counters, UDI of the apparatus 10, Bluetooth MAC address (es) of paired apparatus 10, and other information for future display within the wireless device application or as a log file saved into the memory of the wireless communication device, which may be retrievable without use of the application (e.g., a retrievable or moveable electronic file, such as an ASCII text file or formatted file, such as a comma separated variable (*.csv) file).

The application also preferably provides a user interface to transition the apparatus 10 between software states, allowing a remote control (e.g., through the use of a virtual button) of the apparatus 10 instead of requiring physical interaction with the button 306. For example, the apparatus 10 may transition from the READY, CHARGING, or FAULT states to the SERVICE state or vice versa. When in the SERVICE state, the application preferably allows the user to clear contents of the event log, reset counters, update parameter values, or perform a firmware update on the apparatus 10. The states are discussed in more detail below in.

Figure 10:
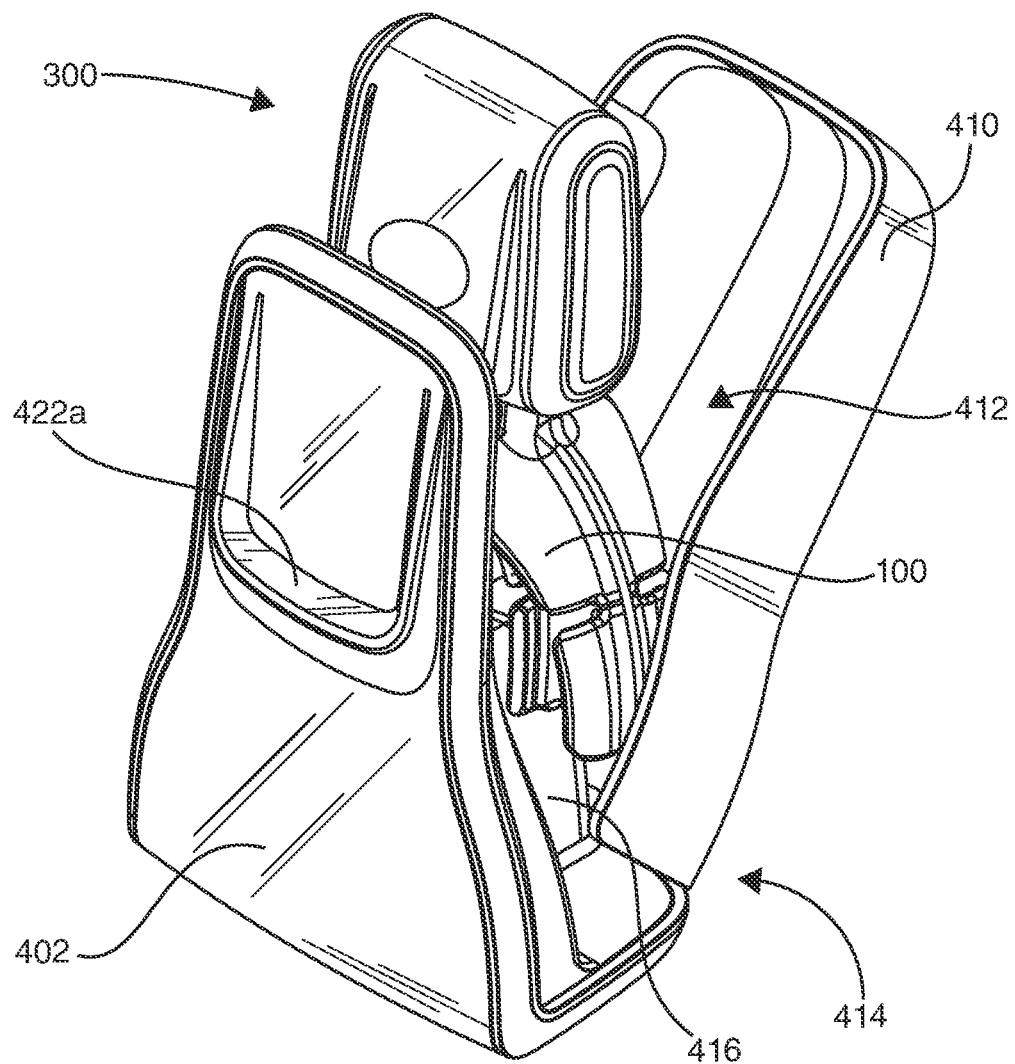
FIG. 10 is a front perspective view of a charging stand/case according to the present invention receiving a mouthpiece/controller according to the present invention.

A charging station 400 according to the present invention preferably comprises a base 402 and a shell 410, as can be seen at least in FIGS. 1 and 10. The base 402 preferably comprises a power input (not shown), such as a USB-C receptacle. The power input is configured to receive input power from a power input source (not shown) (for example, a direct current transformer plugged into a standard electrical outlet providing alternating current). The input power is operatively coupled to a wireless charging coil (not shown) such as that defined by the Qi wireless charging standard.

The base 402 includes a controller support interface 420, including a cradle ridge 422 defining a cradle surface 422a. The cradle ridge 422 is configured to mate with the controller support ridge 322 to help support the controller 300 and to help register the relative positioning of the wireless charging circuitry components. Positioning and registration of the controller 300 relative to the base 402 is preferably further aided by one or more magnets (not shown) secured within the controller housing 310 and the base 402. In this way, when the controller 300 is supported by the controller support interface 420, the inductive charging coil (within the base 402) generates a magnetic field through the shell 410, which is used by a receiving coil (within the controller 300) to charge the battery 302.

The shell 410 is preferably hollow, defining a shell cavity 412 configured to receive the entire controller 300/mouthpiece 100 combination, such as for storage or travel. The shell cavity 412 can be accessed by changing the position of the shell 410, either by removing the shell 410 (if, e.g., a circumferential snap fit cooperation with the base 402 is used) or by pivoting the shell 410 about a hinged pivot point 414, such as a pinned hinge or living hinge. Within the shell cavity 412, and preferably formed integrally with a portion of the base 402, is an arcuate saddle surface 416 configured to receive the U-shaped mouthpiece 100.

To increase electrical conductivity in, across, or to oral tissues adjacent to the electrodes, an ionic or colloidal liquid or gel may be used as a conductive medium to decrease electrical resistance in the mouth. This medium may be placed along any desired areas of desired electrical contact, such as the teeth, gums, or surrounding oral tissues. Examples of such a medium include, but are not limited to, colloidal silver gel, liquid colloidal silver, colloidal copper gel, liquid colloidal copper, colloidal gold gel, liquid colloidal gold, saline gel, liquid saline or any combination thereof.

Colloidal silver, in whole or in combination, has great promise not only in increasing electrical current flow, but also in offering additional bactericidal benefits. Colloidal silver, in concentrations as little as five parts per million, is known to be bactericidal by inhibiting a bacterium's production of adenosine triphosphate.

This conductive medium may also contain dietary supplements including, but not limited to, oil of oregano. Oil of oregano is believed to have many health benefits and may also be microbicidal. Such microbicidal properties would be effective in treating common oral infections and diseases as well as aiding in preventative oral care.

This conductive medium may also contain teeth whitening agents. This would allow for the addition of teeth whitening to the list of cosmetic benefits offered by an embodiment of this invention. A whitening agent that is catalyzed by direct current electricity could be included and may even offer reduced teeth whitening stimulation times when compared with nonelectrically-catalyzed whitening agents.

Artificial or natural flavorings may also be added to this conductive medium to offer a more appealing taste to the user, similar to the method of flavoring dental fluoride treatments. This flavoring would mask any unpleasant tastes from the ingredients of the conductive medium or as well as any taste of the mouthpiece or electrodes themselves.

Thus, at least one embodiment addresses a desired need in the oral hygiene and dental fields to concurrently treat common oral diseases and conditions in a more effective, less invasive, and less expensive manner. These embodiments promote general oral hygiene, reduce oral biofilm, treat periodontal diseases such as gingivitis and periodontitis, kill oral microbes including bacteria and thus preventing cavities and tooth decay, increase vasodilation and blood flow in oral tissues, promote gingival tissue regeneration, foster osteogenesis in the boney structures of the teeth, mouth, and related areas, treat systemic diseases related to oral pathogens, and treat other periodontal and oral maladies through the non-invasive application of weak direct current electricity to the surfaces in the oral cavity.

In some cases, dental procedures can break up oral bacterial colonies found in biofilms and introduce bacteria into the bloodstream causing bacteremia and other infections. It is further contemplated that it may be desirable to utilize a mouthpiece according to the present invention immediately prior to performing a dental procedure. The stimulation apparatus 10 according to the invention may be used by the patient either at home or in the dental office. In this manner, the living bacteria in the patient's mouth, both supra- and sub-gingival, can be reduced prior to the procedure and the risk of bacteremia and other infections will be reduced. For example, and not by way of limitation, the stimulation apparatus 10 may be utilized prior to a dental prophylaxis or a scaling and root planning procedure in a dental office to reduce the risks of introducing bacteria into the patient's blood stream.

The stimulation apparatus 10 may also be utilized following a clinical procedure as prevention for infections, for scenarios including but not limited to post-extraction or post-implantation infection prevention.

In operation, it may be preferable that the number of anodic electrodes is equal to the number of cathodic electrodes, but alternative arrangements are contemplated with different numbers of anodic and cathodic electrodes. It is to be understood that targeted stimulation may be selectively provided, such as may be desirable to treat predetermined gingival areas. To provide targeted stimulation, delivery of electrical current to other portions of the mouth is preferably prevented or reduced mechanically or electrically. As an example, mechanical prevention or reduction may be achieved by particularized arrangement of electrodes, such as providing an anodic or cathodic electrode on a mouthpiece at a first location of gingival tissue that at least partially surrounds (a) a tooth to be removed and replaced with an implant, or (b) an empty tooth socket from which a tooth has already been removed intentionally or by accident, or (c) a portion of a previously placed dental implant. The mechanical prevention or reduction may be further enhanced by providing a cathodic or anodic electrode on the mouthpiece at a second location of (preferably on the opposite side of teeth from first location) gingival tissue that at least partially surrounds (a) the tooth to be removed and replaced with an implant, or (b) an empty tooth socket from which a tooth has already been removed intentionally or by accident, or (c) a portion of a previously placed dental implant. If the two electrodes are provided as described, and no other electrodes are disposed on the mouthpiece, then mechanical reduction of electrical current stimulation is achieved. In this way, a mouthpiece may be customized for a particular user by mechanically arranging electrodes on the mouthpiece to target electrical stimulation towards a dental implant site.

As an example of electrical prevention or reduction of non-targeted electrical current is selective electrode control by the controller. That is, mechanically there may be provided on a mouthpiece a plurality of electrodes spaced about the mouthpiece, as shown and described herein. However, through electrical control of such electrodes, each electrode may have a selectable state to provide stimulation. The selectable electrode state may be anodic, cathodic, or off (e.g., tri-stated). Thus, where targeted electrical current is desired, a first electrode on the mouthpiece may be selected to be an anodic or cathodic electrode. The first electrode position on the mouthpiece may correspond to a first location of gingival tissue that at least partially surrounds (a) a tooth to be removed and replaced with an implant, or (b) an empty tooth socket from which a tooth has already been removed intentionally or by accident, or (c) a portion of a previously placed dental implant. The electrical prevention or reduction of non-targeted electrical stimulation may be further enhanced by a first electrode on the mouthpiece being selected to be a cathodic or anodic electrode (opposite the first electrode). The second electrode position on the mouthpiece may correspond to a second location of (opposite side of teeth from first location) gingival tissue that at least partially surrounds (a) the tooth to be removed and replaced with an implant, or (b) an empty tooth socket from which a tooth has already been removed intentionally or by accident, or (c) a portion of a previously placed dental implant. If the two electrodes are selected as described, and no other electrodes are activated on the mouthpiece (e.g., all other electrodes are turned off or sent into a high impedance, or tri-state, mode), then electrical reduction of electrical current stimulation is achieved. In this way, a mouthpiece may be mechanically standardized for multiple users, but electrically customized to target electrical stimulation towards a dental implant site.

While mechanical and electrical prevention or reduction of stray or non-targeted electrical current has been described with respect to targeting a single dental implant site, it is to be understood that such targeting may be accomplished at multiple implant sites simultaneously or in a time sequenced fashion (e.g., one target site is stimulated for a predetermined time and then a different target site is stimulated for a predetermined amount of time).

Figure 16:
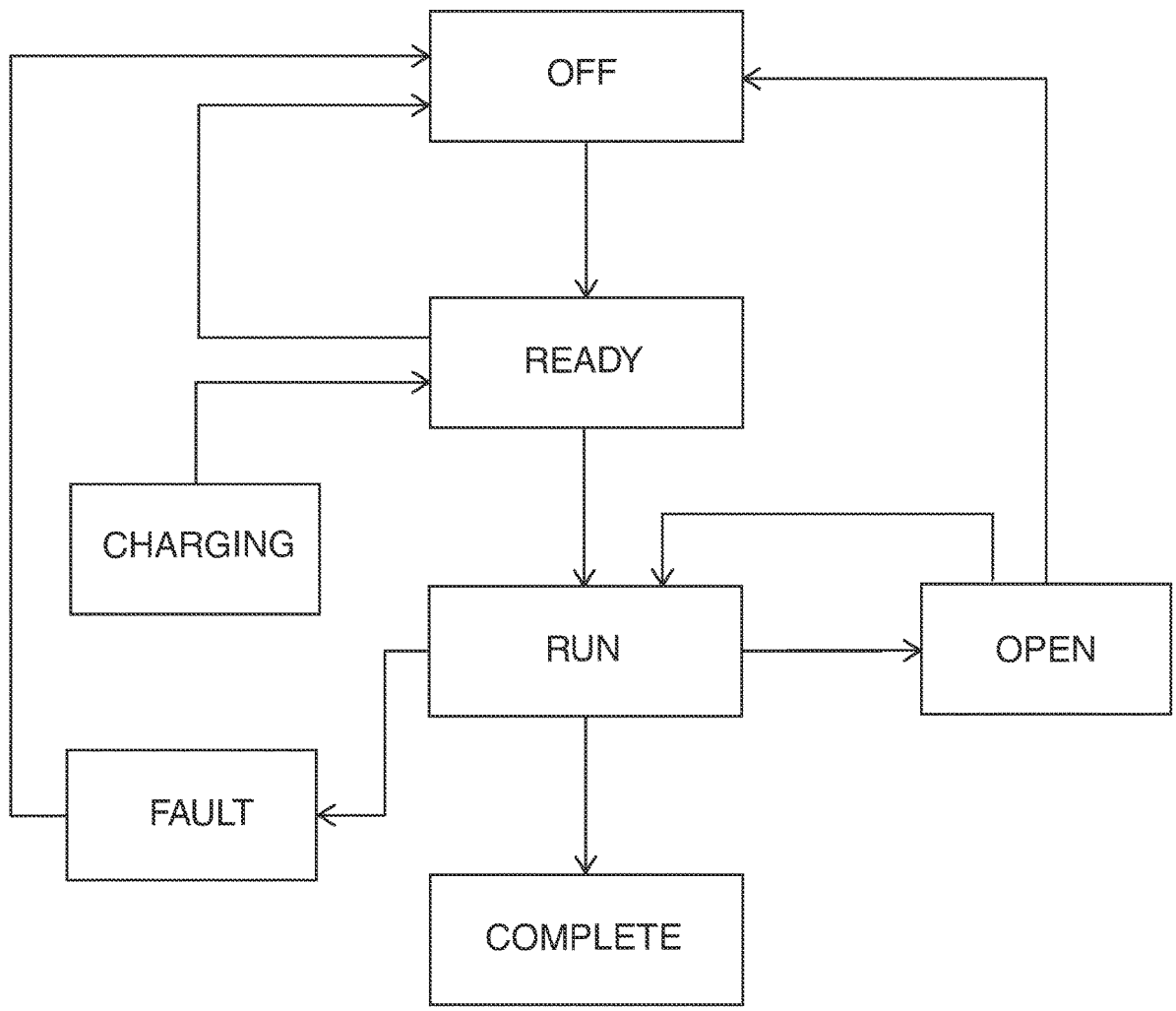
FIG. 16 is a flowchart depicting states of operation or non-operation of a controller according to the present invention.

During operation, the controller 300 generally cycles through and/or between software states, some of which can be seen described in the table provided in FIG. 15A, FIG. 15B, and FIG. 15C. Referring now to FIG. 16, preferred states of the controller 300 can be seen. In an OFF state, there is either no power supplied to the microprocessor or there is a minimal amount of power provided so as to place the microprocessor in a sleep or low-power mode and preferably maintain operation of only a real time clock and perhaps a visual indicator (constant or intermittent). The OFF state can be entered from any other state of the controller if the pushbutton 306 is activated for a predetermined time, such as at least 3 seconds. The OFF state can also be entered from the following states based on a predetermined period of inactivity: OPEN, READY, COMPLETE, LOW BATTERY, CRITICAL_BATTERY or FAULT. The predetermined period of inactivity is used to monitor user activity (i.e., depressing of pushbutton 306) or correction of an OPEN condition. If either of those things happen within an inactivity period, then a different state, besides OFF will be entered from the respective state. The predetermined period of inactivity is preferably a programmable software variable, and is preferably separately programmable with respect to the inactivity (i.e., in the READY, COMPLETE, LOW BATTERY, CRITICAL_BATTERY and/or FAULT states) and the OPEN correction (i.e., current begins flowing again before the expiry of this time). The OFF state is exited by activation of the pushbutton 306 for a predetermined time, such as at least 2 seconds.

The READY state is a state of the controller from which stimulation may be started. The READY state may be entered from the OFF state by activation of the pushbutton 306 for a predetermined time, such as at least 2 seconds. The controller 300 will remain in the READY state until either the pushbutton 306 is activated by a user or a period of inactivity causes the controller to exit the READY state and return to the OFF state.

The RUN state is a state in which delivery electrodes are activated and current is delivered therethrough for a predetermined, programmed time and at a predetermined, programmed current level. The RUN state is entered from the READY state by an activation of the pushbutton 306, either intermittently or for a predetermined period of time. The software causes electrical current delivery (i.e., the controller software will transition to the RUN state) to electrode channels that are activated (i.e., turned on) when the user presses the push button 306 (or a virtual button), preferably only from the READY state. The software monitors a stimulation (e.g., treatment) duration counter which increments at least once every second while current is being delivered. The software compares the stimulation duration counter to the programmed TREATMENT DURATION to determine when current delivery should end. Alternatively, upon entering the RUN state, the software may set an initial value of a decrementing counter to TREATMENT_DURATION, and then monitor that counter to determine when reaches a value of zero, thereby indicating and preferably causing a cessation of current delivery.

Presuming that current is delivered successfully and the stimulation duration counter has expired, the controller software will enter the COMPLETE state, in which electrical current delivery is stopped. Generally, the software will then transition to the OFF state after a predetermined period of time from the COMPLETE state.

Once a stimulation session is complete, or the user otherwise is finished with the device, it may be cleaned by the following process, or equivalent:

1) rinse mouthpiece 100 under cold water for approximately 30 seconds;

2) (occasionally, 2-4 times per month) use a toothbrush to gently scrub the mouthpiece 100 with a mild soap (e.g. dish soap or hand soap) and then rinse the mouthpiece 100 under water to remove soap; and 3) Air dry (e.g., supported on the stand 400).

Additionally or alternatively, the mouthpiece may be occasionally or periodically placed in a solution of denture cleaner for a duration of up to 30 minutes.

If during the RUN state, however, there is an interruption of current delivery (e.g., indicating that the apparatus 10 may have been removed from a user's mouth), as determined by monitoring channel current and/or voltage of one or a combination of channels over a period of time (e.g., if no current is being delivered across all active channels for a period of two seconds), the software will enter the OPEN state, thereby pausing the stimulation duration timer. If electrical current delivery resumes, as determined by monitoring channel current and/or voltage of one or a combination of channels, within a predetermined time period (e.g., prior to the expiration of a counter set to the programmed INACTIVITY_DURATION_OPEN parameter), then the software returns to the RUN state and resumes electrical current delivery to the activated channels and restarts (but does not reset) the paused the stimulation duration timer. If electrical current delivery fails to resume, as determined by monitoring channel current and/or voltage of one or a combination of channels, within the predetermined time period (e.g., not prior to the expiration of a counter set to the programmed INACTIVITY_DURATION_OPEN parameter), then the software returns to the OFF state.

Also during the RUN state, operational faults may occur, such as efficacy (undercurrent) faults and overcurrent faults, thereby transitioning the controller software into a FAULT state, in which electrical current delivery is stopped and a visual and/or aural indication is provided by the controller 300. An efficacy fault may occur if the total current being delivered across all active electrode channels is less than a predetermined, programmable percentage of a target value (MIN_CURRENT_PERCENT, e.g., 75 percent (75%)) for a predetermined, programmable time (MIN_CURRENT_TIME, e.g., 30 seconds). Accordingly, using the exemplary parameter values, if 4 channels are active, and a target current delivery is 125 µA per channel, then an efficacy fault will occur if the total current being delivered, as determined by monitoring channel current of all active channels, falls below 375 µA (125 µA/channel×4 channels× 0.75) for more than 30 seconds. An overcurrent fault may occur when current being delivered on any channel, as determined by monitoring each channel current level, exceeds a predetermined level, such as about 200 µA, or a programmable percentage of a predetermined target current level, such as 110% of the predetermined target current level. The FAULT state preferably requires user intervention to exit and return to the OFF state, such as by requiring depression of the button 306 (or a virtual button) for a predetermined time, such as three seconds.

The CHARGING state is entered whenever the controller 300 is interfaced with a powered charging stand (electrical current delivery to electrode channels being preferably disabled) when the software is in any state except the FAULT state. When the controller 300 is placed on the charging stand 400 in the FAULT state, it preferably will remain in the FAULT state but will allow the battery to charge. The controller 300 preferably does not exit the FAULT state automatically when removed from the charging stand 400, if it was in the FAULT state when placed thereon. Rather, the FAULT state remains, thereby preferably requiring user intervention to exit and return to the OFF state, such as by requiring depression of the button 306 (or a virtual button) for a predetermined time, such as three seconds.

Other states than those shown in FIG. 11 may be defined and utilized, such as a LOW BATTERY state, a CRITICAL BATTERY state, and a SERVICE state. The circuitry monitors available voltage at the battery 302. In LOW and CRITICAL BATTERY states, electrical current delivery is deactivated, and the user is informed, through visual and/or aural indicators of the battery state. A LOW BATTERY state may be entered if the voltage of the battery 302 is less than a first predetermined battery run value (e.g., 3.5 volts) when a user attempts to enter the RUN state. The LOW BATTERY state may also be entered upon transition between the RUN state and the COMPLETE state, if the voltage of the battery 302 is less than a second predetermined battery run value (e.g., 3.6 volts), which is preferably higher than the first predetermined battery run value. A CRITICAL BATTERY state is preferably entered if the voltage of the battery 302 is less than a lower predetermined value than the low battery predetermined value (e.g., 3.1 volts) in any state, except in the FAULT state. This provides an ability for event logging to non-volatile memory prior to a brownout of the microprocessor, thereby shutting the system down in a controlled fashion. If the controller 300 is powered down (e.g., by depressing the button 306 for a predetermined time) while in the CRITICAL BATTERY state, it will preferably subsequently power on in that same state if it has not been placed on the charger 400 in the meantime.

The SERVICE state may be entered through the use of a wireless communication device application in communication with the controller 300, thereby allowing parameters to be programmed through a user interface provided thereon. The SERVICE state may be entered from any of the READY, CHARGING, or FAULT states. The SERVICE state may provide the following functionality:

viewing and changing programmable parameters (e.g., those listed in FIGS. 12A-B);

viewing counter values (e.g., of one or more counters listed in FIGS. 13A-B) as provided by the controller 300;

resetting one or more counter values on the controller 300 (and/or archiving counter labels and values on the paired wireless communication device, during or after pairing);

viewing the event log (e.g., of one or more events listed in FIG. 14) as provided by the controller 300;

clearing one or more events from the event log on the controller 300 (and/or archiving the event log on the paired wireless communication device, during or after pairing); and/or nondestructive, preferably authenticated, updates of firmware on the controller 300.

Once data is obtained from the controller 300, it may be forwarded by the wireless communication device manually or automatically over a wireless network to then be stored remotely therefrom, such as on a remote data storage device networked with the wireless communication device (cloud storage or remote server, which may be associated with the manufacturer and/or seller of the apparatus 10, a care provider (e.g., dentist, hygienist, administrative staff), an insurance company, or the user (or user's guardian).

When a user has completed any of the above tasks (i.e., when the user wants to exit the SERVICE state), the user may do so through the use of the application on the mobile wireless device. From the SERVICE state, the controller transitions back to READY if the apparatus 10 is not on an active charger 400, to CHARGING if on an active charger 400, or FAULT if the SERVICE state was entered from the FAULT state.

Prevention of Systemic Disease

It is contemplated that a mouthpiece according to the present invention may be used to prevent or treat systemic diseases as will be outlined in more detail below. The method according to the present invention has been shown to be effective in reducing the amount of oral bacteria, specifically *F. nucleatum*, *P. gingivalis*, and *S. oralis*.

1. Cardiovascular Disease

It is contemplated that use of a mouthpiece according to the present invention may be used to reduce microbial burdens caused by the translocation of oral bacteria, including but not limited to *S. oralis*, *P. gingivalis*, and *F. nucleatum*, from the gingival tissues to the rest of the body and also decrease the amount of inflammatory mediators produced by oral bacteria. Further, by reducing *F. nucleatum*, it is contemplated that the ability of *P. gingivalis* to invade host cells will be lessened and thus diminishing the development of bacteremia that has been linked with the initiation/worsening of atherosclerosis and coronary heart disease.

It is contemplated that a mouthpiece according to the present invention may be used according to a predetermined stimulation regimen to prevent, treat and/or mitigate cardiovascular disease. In the predetermined stimulation regimen, the patient will wear a mouthpiece according to the present invention for a predetermined amount of time at a predetermined current level and at predetermined time intervals. It is further contemplated that the specific stimulation regimen may be determined based on the bacterial levels present in a patient. According to one embodiment of the invention, the stimulation regimen would consist of a patient wearing a mouthpiece according to the present invention for 20 minutes once per day at a current level of 500 μA. For acute cardiovascular conditions, this stimulation may continue on a daily basis until the conditions is resolved. For chronic cardiovascular disease, this stimulation may be repeated a few times a week on a continuing basis.

2. Still Birth

It is further contemplated that stimulation sessions with a mouthpiece according to the present invention according to a predetermined stimulation protocol would reduce the oral population of *F. nucleatum* associated with periodontal disease and thus prevent, treat and/or mitigate still birth. In turn, this reduction would lessen the likelihood of *F. nucleatum* translocating from the oral cavity into the bloodstream, where it could then migrate into the placenta and colonize. It is contemplated that a mouthpiece according to the present invention may be used according to a predetermined stimulation regimen to prevent still birth. In the predetermined stimulation regimen, the patient will wear a mouthpiece according to the present invention for a predetermined amount of time at a predetermined current level and at predetermined time intervals. It is further contemplated that the specific stimulation regimen may be determined based on the bacterial levels present in a patient. According to one embodiment of the invention, the stimulation regimen would consist of a patient wearing a mouthpiece according to the present invention for 20 minutes once per day at a current level of 500 μA for the duration of the pregnancy. The stimulation parameters outlined above have been demonstrated to be highly efficient at reducing levels of *S. oralis* and *F. nucleatum* at inoculation sizes of $10^7$ colony-forming units (CFU)

3. Diabetes

It is contemplated that a mouthpiece according to the present invention according to a predetermined stimulation protocol may be used to prevent, treat and/or mitigate diabetes by causing a reduction of *S. oralis* in the oral cavity and consequently reduce the amount of serum markers of inflammation produced by bacterial infections. In the predetermined stimulation regimen, the patient will wear a mouthpiece according to the present invention for a predetermined amount of time at a predetermined current level and at predetermined time intervals. It is further contemplated that the specific stimulation regimen may be determined based on the bacterial levels present in a patient. According to one embodiment of the invention, the stimulation regimen would consist of a patient wearing a mouthpiece according to the present invention for 20 minutes once per day at a current level of 500 μA to effectively reduce oral levels of *S. oralis* that in turn will lower the amount of systemic inflammatory markers. This stimulation may be repeated multiple times a week on an ongoing basis to help reduce inflammatory markers.

4. Pyogenic Liver Abscess

It is contemplated that a mouthpiece according to the present invention according to a predetermined stimulation protocol may be used to prevent, treat and/or mitigate pyogenic liver abscess by causing a reduction of *F. nucleatum*. Specifically, it is contemplated that stimulation sessions with a mouthpiece according to the present invention would reduce bacterial levels and may stop *F. nucleatum* and other oral bacteria species from traveling to the liver and reduce overall bacteremia. In the predetermined stimulation regimen, the patient will wear a mouthpiece according to the present invention for a predetermined amount of time at a predetermined current level and at predetermined time intervals. It is further contemplated that the specific stimulation regimen may be determined based on the bacterial levels present in a patient. According to one embodiment of the invention, the stimulation regimen would consist of a patient wearing a mouthpiece according to the present invention for 20 minutes once per day at a current level of 500 μA to effectively reduce oral levels of *F. nucleatum* which may prevent any bacteria from being transported from the oral cavity systemically. This stimulation may be repeated multiple times per week until the abscess is reduced.

5. Osteomyelitis

It is contemplated that a mouthpiece according to the present invention according to a predetermined stimulation protocol may be used to prevent, treat and/or mitigate osteomyelitis by causing a reduction of *F. nucleatum*. In the predetermined stimulation regimen, the patient will wear a mouthpiece according to the present invention for a predetermined amount of time at a predetermined current level and at predetermined time intervals. It is further contemplated that the specific stimulation regimen may be determined based on the bacterial levels present in a patient. According to one embodiment of the invention, the stimulation regimen would consist of a patient wearing a mouthpiece according to the present invention for 20 minutes per stimulation session at a current level of 500 μA to effectively reduce oral levels of *F. nucleatum* bacteria and prevent any bacteria from being transported from the oral cavity systemically. This stimulation may be used in conjunction with or separate from standard antibiotic-based treatments for osteomyelitis. When used in conjunction with antibiotics, stimulation sessions will normally take place within a period of 29 to 42 days. When used separately from antibiotics, this stimulation may be used once a day for a few months for acute conditions, or a few times a week on a continuing basis for chronic conditions.

6. Arthritis

It is contemplated that a mouthpiece according to the present invention according to a predetermined stimulation protocol may be used to prevent, treat and/or mitigate arthritis by causing a reduction of *F. nucleatum*. In the predetermined stimulation regimen, the patient will wear a mouthpiece according to the present invention for a predetermined amount of time at a predetermined current level and at predetermined time intervals. It is further contemplated that the specific stimulation regimen may be determined based on the bacterial levels present in a patient. According to one embodiment of the invention, the stimulation regimen would consist of a patient wearing a mouthpiece according to the present invention for 20 minutes once per day at a current level of 500 μA to effectively reduce oral levels of *F. nucleatum* bacteria and prevent any bacteria from being transported from the oral cavity and translocating to the synovial fluid and reducing the associated inflammation. This stimulation may be repeated multiple times per week on a continual basis for this type of chronic condition.

Reducing Biofilm and Preventing Biofilm Formation

It is contemplated that a mouthpiece according to the present invention according to a predetermined stimulation protocol may be used to prevent, treat and/or mitigate oral biofilm by causing a reduction of *F. nucleatum*, *P. gingivalis*, and/or *S. oralis*, all of which are involved in oral biofilm formation. In the predetermined stimulation regimen, the patient will wear a mouthpiece according to the present invention for a predetermined amount of time at a predetermined current level and at predetermined time intervals. It is further contemplated that the specific stimulation regimen may be determined based on the bacterial levels of specific bacterial species present in a patient. According to one embodiment of the invention, the stimulation regimen would consist of a patient wearing a mouthpiece according to the present invention for 20 minutes once per day at a current level of 500 μA to effectively reduce oral levels of *F. nucleatum* bacteria to prevent further biofilm formation caused by *F. nucleatum* and to reduce the viability of existing biofilm colonies of *F. nucleatum*.

According to another embodiment of this invention, the stimulation regimen would consist of a patient wearing a mouthpiece according to the present invention for 20 minutes once per day at a current level of 50 μA to effectively reduce oral levels of *P. gingivalis* bacteria to prevent further biofilm formation caused by *P. gingivalis* and to reduce the viability of existing biofilm colonies of *P. gingivalis*.

Furthermore, according to another embodiment of this invention, the stimulation regimen would consist of a patient wearing a mouthpiece according to the present invention for 20 minutes once per day at a current level of 500 μA to effectively reduce oral levels of *S. oralis* bacteria to prevent further biofilm formation caused by *S. oralis* and to reduce the viability of existing biofilm colonies of *S. oralis*.

These stimulation sessions for biofilm reduction and prevention may be repeated on a daily basis for three to six weeks for acute biofilm-based issues or may be repeated once or more per week on a continuing basis for chronic biofilm issues.

Treatment and/or Prevention of Peri-Implantitis

Peri-implantitis is generally inflammation of oral tissue in physical contact with, surrounding, or otherwise in proximity to, and occurring after, placement of a dental implant. This inflammation may be reduced or prevented using methods according to the present invention. Methods may be performed before and/or after a dental implant surgical procedure of dental implant placement or replacement.

A method of reducing a likelihood of peri-implantitis involves, prior to a dental implant being placed or replaced partially or in its entirety, applying or directing electrical current to gingiva tissue near or at an oral site of future implantation. While electrical current may be distributed elsewhere throughout oral tissue, at least 6 μA and more preferably at least approximately 50 μA of electrical current (and preferably no more than 300 μA) is delivered to the gingiva tissue near or at a predetermined oral site of future implantation. A pre-surgery stimulation regimen may consist of approximately twenty minutes of electrical stimulation per day for one to fourteen days prior to a dental implant surgical procedure.

A method of reducing a likelihood of peri-implantitis (if it has not yet begun) or reducing peri-implantitis (if it has already begun) involves, after a dental implant has been placed or replaced partially or in its entirety, applying or directing electrical current to gingiva tissue near or at an oral site of implantation. While electrical current may be distributed elsewhere throughout oral tissue, at least 6 μA and more preferably at least approximately 50 μA of electrical current (and preferably no more than 300 μA) is delivered to the gingiva tissue near or at a predetermined oral site of implantation. A post-surgery stimulation regimen may consist of approximately twenty minutes of electrical stimulation per day for one to fourteen days after a dental implant surgical procedure, or until desired inflammation reduction has occurred.

While the pre-surgery and post-surgery methods have been separately described for clarity, it is to be understood that either or (preferably) both methods may be utilized for a particular patient, or user of the mouthpiece.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention.

We claim:

1. A system comprising:
    a controller having a housing containing a variable direct current power supply, the power supply capable of delivering approximately 1 to 500 microamperes;
    a mouthpiece configured to be received in a human mouth, the mouthpiece comprising at least one U-shaped channel;
    a plurality of exposed electrodes supported by the mouthpiece and coupled to the direct current power source; and
    a neck portion electrically coupling the direct current power supply to the mouthpiece and physically coupling the housing to the mouthpiece,
    wherein the electrical coupling in the neck portion is achieved by a plurality of electrically conductive pins inserted into and substantially surrounded by traces of electrically conductive silicone.

2. A system according to claim 1, wherein a first of the plurality of exposed electrodes is a cathode electrode disposed on a first side of a first of the at least one U-shaped channel and a second of the plurality of exposed electrodes is an anode electrode disposed on a second side of the first channel.

3. A system according to claim 1, wherein the mouthpiece comprises two U-shaped channels, wherein one channel is configured to receive one or more maxillary teeth of a human and the other channel is configured to receive one or more mandibular teeth of the human.

4. A system according to claim 3, wherein the controller comprises electronic circuitry disposed in the housing, the circuitry being configured to at least one of manipulate and monitor at least one of duration and intensity of current provided by the power source to each electrode.

5. A system according to claim 4, wherein the controller further comprises a user input interface and a user feedback interface.

6. A system according to claim 5, wherein the controller is configured to store one or more counter values and an event log in non-volatile memory.

7. A system according to claim 6, wherein the event log can store a minimum of two thousand event occurrences, including a timestamp associated with each.

8. A system according to claim 1, wherein the variable direct current power supply comprises a rechargeable lithium-ion battery.

9. A system according to claim 8, wherein the system further comprises a charging station capable of physically supporting the controller housing and inductively recharging the rechargeable lithium-ion battery.

10. A system according to claim 9, wherein the charging station comprises a hinged cover, which is configured to enclose the controller and mouthpiece.

11. A system according to claim 6, wherein the system further comprises a mobile wireless communication device capable of physical layer communication with the controller, the wireless device further including a software application capable of software layer communication with the controller.

12. A system according to claim 11, wherein the controller is capable of transmitting the counter values and event log to the wireless device the application.

13. A system according to claim 12, wherein the controller transmits the counter values and event log upon at least one of an occurrence of a predetermined event, an expiration of a predetermined time period, and at a predetermined time of day.

14. A system according to claim 12, wherein the application is configured to display simultaneously at least one transmitted counter value and event log.

15. A system according to claim 12, wherein the application is configured to allow storage of the transmitted counter values and event log to non-volatile memory in the wireless device.

16. A system according to claim 11, wherein the application is configured to provide firmware updates to the controller.

17. A system according to claim 1, wherein the mouthpiece is formed by a process comprising the steps of:
   a first injection molding procedure using the conductive silicone material to form the traces and the electrodes to form a conductive skeleton; and
   a second injection molding procedure using insulative silicone material to encapsulate at least a portion of each trace.

18. A system according to claim 17, wherein the second injection molding procedure is performed after the first injection molding procedure.

* * * * *